(12) United States Patent
Jarvest et al.

(10) Patent No.: US 6,579,981 B1
(45) Date of Patent: Jun. 17, 2003

(54) ANTIVIRAL GUANINE DERIVATIVES

(75) Inventors: Richard Lewis Jarvest, Surbiton (GB); Michael Raymond Harnden, Horsham (GB)

(73) Assignee: Novartis International Pharmaceutical Ltd., Hamilton (BM)

( * ) Notice: Subject to any disclaimer, the term of this patent is extended or adjusted under 35 U.S.C. 154(b) by 0 days.

(21) Appl. No.: 08/311,291

(22) Filed: Sep. 23, 1994

Related U.S. Application Data

(63) Continuation of application No. 07/918,111, filed on Jul. 20, 1992, now abandoned, which is a continuation of application No. 07/607,403, filed on Oct. 31, 1990, now abandoned, which is a division of application No. 07/085,216, filed on Aug. 12, 1987, now Pat. No. 5,075,445, which is a continuation of application No. 06/641,300, filed on Aug. 16, 1984, now abandoned.

(30) Foreign Application Priority Data

| Sep. 21, 1908 | (GB) | 8325271 |
| Aug. 18, 1983 | (GB) | 8322199 |
| Mar. 30, 1984 | (GB) | 8408322 |

(51) Int. Cl.$^7$ .............. C07D 473/18; A61K 31/522; A61P 31/22
(52) U.S. Cl. .............. 544/263.38; 544/276
(58) Field of Search .............. 544/276, 277; 514/262, 263.38

(56) References Cited

U.S. PATENT DOCUMENTS

| 4,495,190 A | * | 1/1985 | Hagborg et al. | 514/262 |
| 4,845,084 A | * | 7/1989 | Hannah | 514/81 |
| 4,942,166 A | * | 7/1990 | Marnden et al. | 514/262 |
| 5,075,445 A | * | 12/1991 | Jarvest et al. | 544/277 |

OTHER PUBLICATIONS

Nadler, Comprehensive Therapy 23, p104, 1997.*
"Healthanswers", http://www.healthanswers.com/database/ami/converted/000591.html, 1997.*
Andersson, Scand J. Infectious Diseases Suppl 100: 72–82, 1996.*
Savage et al, Q J Med 90, 497, 1997.*
Boyd et al, Antiviral CHem. and Chemotherapy, vol. 4 Suppl 1, p 3–11, 1993.*
Bacon, Antimicrobial Agents and Chemotherapy vol. 39, No. 7, p 1599–1602, 1995.*
Spruance, JAMA vol. 277, p 1374–1379, 1997.*
Physicians Desk Reference, pp. 1219–1226, 1996.*
Neyts, Antimicrobial Agents and Chemotherapy, 41, 2754, Dec. 1997.*
Neyts, Antimicrobial Agents and Chemotherapy, 42, 170, Jan. 1998.*
Smee, Antimicrobial Agents and Chemotherapy, 23, 676, May 1983.*
Soike, Antimicrobial Agents and Chemotherapy, 20, 291, Sep. 1981.*
Daniel, Antimicrobial Agents and Chemotherapy, 18, 622, Oct. 1980.*
Biron, Antimicrobial Agents and Chemotherapy, 18, 443, Sep. 1980.*
Boyd, Antimicrobial Agents and Chemotherapy, 31, 1238, Aug. 1987.*
Collins, J. of Antimicrobial Chemotherapy 12, Suppl B, 19, 1983.*
Tyms, J. of Antimicrobial Chemotherapy 8, 65, 1981.*
Smith, Am. J Vet Res 44, 1032, 1983.*
Elion, Proc. Natl. Acad Sci. 74, 5716, Dec. 1977.*
Field, Proc. Natl. Acad Sci. 80, 4139, Jul. 1983.*
Schaeffer Nature 272, 583, 1978.*
Boyd, Antiviral Chem & Chemotherapy 4, Suppl 1, 3–11, 1993.*
Black, Virus Research 52, 25, 1997.*
Reymen, Antiviral research 28, 343, 1995.*
Bandit et al, Synthetic Communications vol. 2 (6) 345–351(1972).*

* cited by examiner

*Primary Examiner*—Mark L. Berch
(74) *Attorney, Agent, or Firm*—Thomas R. Savitsky

(57) ABSTRACT

A compound of formula (I)

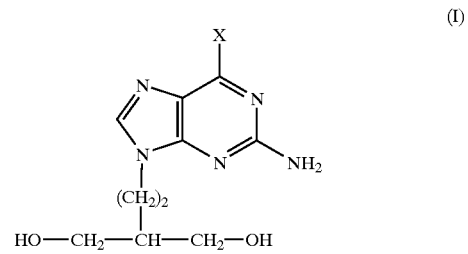

(I)

or a salt or acyl derivative thereof, in which X represents chlorine, $C_{1-6}$ alkoxy, phenoxy, phenyl $C_{1-6}$ alkoxy, $NH_2$, —OH or —SH, is useful in treating viral infections.

50 Claims, No Drawings

ANTIVIRAL GUANINE DERIVATIVES

This is a continuation of application Ser. No. 7/918,111, filed Jul. 20, 1992, abandoned which is a continuation of U.S. Ser. No. 07/607,403, filed on Oct. 31, 1990, abandoned which is a divisional application of U.S. Ser. No. 07/085,216, U.S. Pat. No. 5,075,445 filed on Aug. 12, 1987, which is a continuation application of U.S. Ser. No. 06/641,300, filed on Aug. 16, 1984 abandoned.

The present invention relates to compounds having anti-viral activity, processes for their preparation and pharmaceutical compositions containing them.

The compound 9-(4-hydroxy-3-hydroxymethylbut-1-yl) guanine of formula (A)

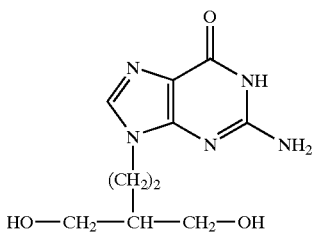

(A)

is disclosed in Synthetic Communications, 2(6), 345–351 (1972) but no pharmaceutical activity has been indicated for the compound in this or any other published document. We have repeated the synthesis of the compound as described in the above publication, and have shown that the product is a mixture of the compound of formula (A), its monobenzyl ether and its dibenzyl ether, this mixture having a melting point and uv spectrum in agreement with those reported in the publication for the supposedly 'pure' compound of formula (A). Our analysis of the product produced by the above synthesis showed that it contained 45–50% by weight of the compound of formula (A), 45–50% by weight of the monobenzyl ether and 5% or less by weight of the dibenzyl ether.

By different synthetic routes, we have prepared the compound of formula (A) in a substantially pure form and have found that it has anti-viral activity. This activity is also shown by certain derivatives of the compound of formula (A).

According to the present invention there is provided a compound of formula (I)

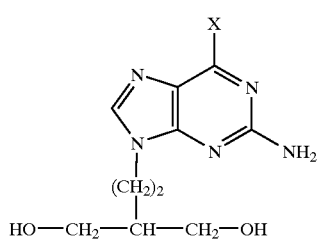

(I)

or a salt, phosphate ester or acyl derivative thereof, in which X represents chlorine, straight or branched chain $C_{1-6}$ alkoxy, preferably methoxy, phenoxy, phenyl $C_{1-6}$ alkoxy, —$NH_2$, —OH or —SH with the proviso that, when X is —OH, the compound of formula (I) is in a purity state of greater than 50% by weight, of pure compound.

The term 'acyl derivative' is used herein to include any derivative of the compounds of formula (I) in which one or more acyl groups are present. Such derivatives include biological precursors of the compounds of formula (I) in addition to those derivatives which are per se biologically active.

Examples of acyl derivatives of the compounds of formula (I) are those wherein one or both of the hydrogens in the acyclic OH groups, and/or one of the hydrogen atoms in the —$NH_2$ group, are replaced by

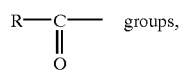 groups, wherein R is hydrogen or an alkyl, aryl, aralkyl or heterocyclyl group.

Examples of alkyl groups R include straight and branched chain groups containing up to 18 carbon atoms, preferably up to 6 carbon atoms. Particular examples are methyl, ethyl, t-butyl and pentyl.

Examples of aryl groups R include phenyl optionally substituted with up to five preferably up to three groups.

Examples of aralkyl groups R include phenyl-$C_{1-6}$ alkyl groups such as benzyl.

Examples of heterocyclyl groups R include single or fused rings containing one or two hetero-atoms in each ring, selected from oxygen, nitrogen and sulphur.

Examples of phosphate esters of the compounds of formula (I) include those where one or both of the acyclic —OH groups are replaced by

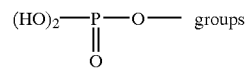 groups or salts thereof, or where the two —OH groups are replaced by a bridging

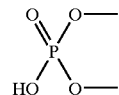

group

Salts, phosphate esters and acyl derivatives of the compounds of formula (I) are preferably pharmaceutically acceptable, but non-pharmaceutically acceptable compounds are also within the scope of the present invention, since these are useful as intermediates in the preparation of pharmaceutically acceptable compounds.

The compounds of formula (I) are defined herein as including tautomers of formula (I), wherein the —OH and —SH substituents are replaced by =O and =S substituents respectively.

A particular group of compounds of the invention are those of formula (II)

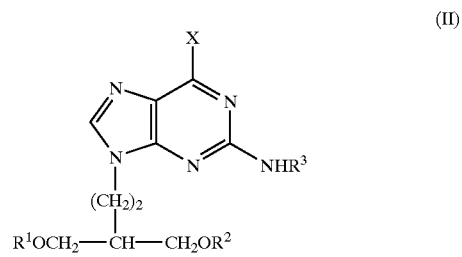

(II)

or pharmaceutically acceptable salts thereof, in which X is as defined in formula (I), and each of $R^1$, $R^2$ and $R^3$ represents hydrogen or an acyl group of formula $$R^4-\underset{\underset{O}{\|}}{C}-,$$

in which $R^4$ is $C_{1-18}$ alkyl or imidazolyl, or $R^1$ or $R^2$ represents a phosphate ester group of formula $$(HO)_2-\underset{\underset{O}{\|}}{P}-,$$

or $R^1$ and $R^2$ together represent a $$\underset{OH}{\overset{O}{\underset{}{\diagdown}}}\!\!\!\!\overset{\diagup}{P}\diagdown$$

bridging group.

Subject to the aforementioned purity proviso in relation to compounds of the invention, a preferred compound of the present invention is the compound of formula (A)

(A)

[structure of compound (A): purine with oxo and NH₂ substituents, N-(CH₂)₂-CH(CH₂OH)₂ side chain]

HO—CH₂—CH—CH₂—OH
         |
      (CH₂)₂ or a salt or acyl derivative therof.

In a further aspect of the invention there is provided a compound of formula (A) in a purity state of greater than 60% preferably greater than 80% more preferably greater than 90% and particularly preferably more than 95% by weight of pure compound.

In yet a further aspect of the invention, there is provided an isolated, substantially completely pure compound of formula (A), or a pharmaceutically acceptable salt thereof.

The invention also provides a compound of formula (A) in crystalline form having a melting point of 275–277° C.

The compounds of the present invention have antiviral activity, and are potentially useful in the treatment of infections caused by herpes viruses, such as herpes simplex type 1, herpes simplex type 2 and varicella zoster viruses.

Accordingly, the present invention also provides a compound of formula (I) or a pharmaceutically acceptable salt, phosphate ester or acyl derivative thereof, for use as an active therapeutic substance, and in particular for use in the treatment of viral infections. In this aspect of the invention, the compounds of formula (I) are not subject to the aforementioned purity proviso.

Examples of pharmaceutically acceptable salts of the compounds of formula (I) are those formed with organic bases, preferably with amines such as ethanolamines or diamines; and alkali metals, such as sodium and potassium; and acid addition salts formed with a pharmaceutically acceptable acid such as hydrochloric acid, orthophosphoric acid and sulphuric acid.

The compound of formula (A) or a salt thereof may be prepared by converting the group X in a compound of formula (III).

(III)

[structure of compound (III): purine with X substituent and Y substituent, N-(CH₂)₂-CH(CH₂OR^a)(CH₂OR^b) side chain]

$R^bOCH_2$—CH—$CH_2OR^a$
         |
      (CH₂)₂ in which X, excluding —OH, is as defined in formula (I); $R^a$ and $R^b$, which may be the same or different, are each hydrogen or O— protecting groups, preferably acyl groups; and Y is chlorine or —$NHR^c$, in which $R^c$ is hydrogen or acyl, to an —OH group by means of hydrolysis, preferably acid hydrolysis, when X is other than $NH_2$, or, when X is —$NH_2$, by means of a deaminase reaction, or when Y is chlorine and X is —OH, converting Y to a —$NH_2$ group by reaction with ammonia under pressure in accordance with known methods, and subsequently, if desired, converting the compound of formula (A) to a salt thereof by treatment with an acid or base.

Acyl groups $R^a$, $R^b$ and $R^c$ may be those of formula $$R-\underset{\underset{O}{\|}}{C}-R^c$$

as hereinbefore defined.

Examples of groups $R^a$ and $R^b$ in formula (III) are acetyl and cyclic acetal such as isopropylidene, is preferably acetyl or hydrogen.

A preferred process for preparing the compound of formula (A) comprises treating a compound of formula (III) in which X is chlorine, Y is —$NH_2$ and $R^a$ and $R^b$ are each acetyl, with aqueous mineral acid, preferably hydrochloric acid.

Compounds of formulae (III) when each of $R^a$, $R^b$ and $R^c$ is hydrogen or acyl, are themselves compounds of the invention, having the additional utility as intermediates for the preparation of the compound of formula (A).

In a further aspect of the invention, compounds of formula (I) or acyl derivatives thereof, together with, compounds of formula (III), may be prepared by treating a compound of formula (IV).

(IV)

[structure of compound (IV): purine with X and Y substituents, NH]

in which X is as defined in formula (I) and Y is as defined in formula (III), with a compound of formula (V)

(V)

$R^aOCH_2$
         ⟩CH—(CH₂)₂—Z
$R^bOCH_2$ in which $R^a$ and $R^b$ are as defined in formula (III) and Z is a leaving group such as Cl, Br, or I, preferably Br.

Compounds of formula (IV) are either known compounds or can be made from known compounds by known methods.

Compounds of formula (V) in which Z is bromine may be prepared by brominating a compound of formula (VI).

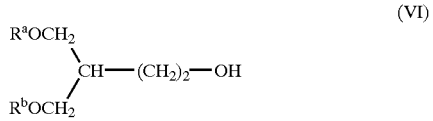

preferably by treatment with carbon tetrabromide and triphenylphosphine in an organic, aprotic solvent, such as dimethylformamide.

Compounds of formula (V) in which Z is Cl or I may be prepared in an analogous manner.

Compounds of formula (VI) in which $R^a$ and $R^b$ are identical may be prepared according to the following schematic process.

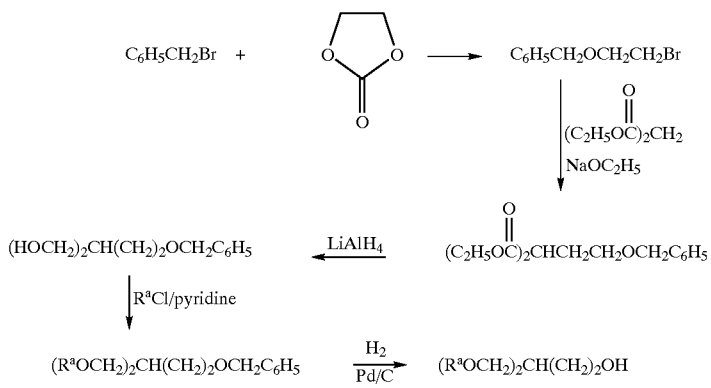

Acyl derivatives of compounds of formula (I) may also be prepared by acylating an optionally protected compound of formula (I) in accordance with conventional acylating processes known in the art, and where necessary, deprotecting the resulting product.

The acylation reaction may be carried out by using an acylating agent containing a

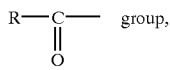

wherein R is as hereinbefore defined.

In a particular aspect of this process, the acylating agent contains the

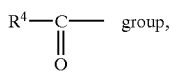

in which $R^4$ is $C_{1-18}$ alkyl, or is N,N'-carbonyldiimidazole.

Examples of acylating agents suitable for the above process are carboxylic acids, acid halides or acid anhydrides, preferably anhydrides or acids.

When the acylating agent is a carboxylic acid, a coupling agent such as dicyclohexylcarbodiimide should be included, but this is not necessary when the acylating agent is an acid anhydride.

The acylation reaction may produce a single acyl derivative of a compound of formula (I), or a mixture of derivatives, depending on a number of factors, such as the relative amounts and chemical natures of reactants, the physical conditions of the reaction, and the solvent system. Any mixture produced in this way may be separated into its pure components using standard chromatographic techniques.

The above described acylation process of the invention can yield mono-, di-, or tri-acylated derivatives of compounds of formula (I) according to the form of protection/deprotection utilised. The following are examples of products obtained by different methods:

(a) Di-acylated derivatives of the two acyclic —OH groups may be obtained by direct acylation of unprotected compounds of formula (I) or acylation of protected intermediates of compounds of formula (I) in which the —$NH_2$ group is protected by, for example, a monomethoxytrityl group, and subsequent deprotection by treatment with acid.

(b) Mono-acylated derivatives of one of the acyclic —OH groups may be obtained by acylation of protected intermediates of compounds of formula (I) in which the —$NH_2$ group and the other acyclic —OH group are both protected by, for example, monomethoxytrityl groups, and subsequent deprotection by acid treatment.

(c) Mono-acylated derivatives of the $NH_2$ group may be obtained by acylation of protected intermediates of compounds of formula (I) in which both acyclic —OH groups are protected by, for example trimethylsilyl groups, and subsequent deprotection.

The various protected intermediates of compounds of formula (I) may be prepared in accordance with standard procedures by, for example, treatment of the compounds with monomethoxytrityl chloride (for processes (a) and (b)) or with chlorotrimethylsilane (for process (c)).

Protected intermediates of compounds of formula (I) may also be used to prepare phosphate esters of the compounds.

Accordingly, in a further process aspect of the invention, there is provided a process for preparing a mono-phosphate ester of a compound of formula (I) which comprises treating a protected intermediate of the compound of formula (I) in which one of the acyclic —OH groups and the —$NH_2$ group are protected, preferably by monomethoxytrityl groups, with cyano ethyl phosphoric acid and subsequently deprotecting the resultant product by treatment with acid, preferably acetic acid.

If desired, the reaction product after treatment with cyano ethyl phosphoric acid is treated with aqueous ammonia, which yields the ammonium salt of the phosphate ester as the final product.

Compounds of formula (I) or salts thereof may also be prepared by hydrolysing the 1,3-dioxane ring of a compound of formula (VII).

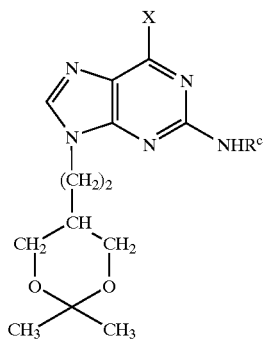

(VII)

in which X is as defined in formula (I) and $R^c$ is as defined in formula (III), provided that $R^c$ is not acyl when X is other than OH, and subsequently, if desired, converting the compound of formula (I) thus formed to a salt by treatment with an acid or base.

When $R^c$ is an acyl group, a basic N-deprotection step is required to form the compound of formula (A). This can be carried out prior to or after hydrolysis by treatment with, for example, (i) a solution of NaOMe in $CH_3OH$ or (ii) a solution of $NH_3$ in $CH_3OH$.

Preferably the hydrolysis of compounds of formula (VII) is carried out in acid medium. The compounds of formula (VII) in which X is alkoxy, phenoxy, phenylalkoxy or —SH are conveniently prepared in situ by reacting the compound of formula (VII) in which X is chlorine with an additional reactant containing an $X^1$ substituent, wherein $X^1$ is alkoxy, phenoxy, phenylalkoxy or sulphur. These intermediates can then be hydrolysed to compounds of formula (I) without isolating them from the reaction mixture.

The additional reactant containing the $X^1$ moiety may be a sodium alkoxide, phenoxide or phenylalkoxide, or sodium hydrosulphide (when $X^1$ is sulphur).

Acid hydrolysis of a compound of formula (VII) in which X is chlorine willyield a compound of formula (I) in which X is chlorine, or a compound of formula (A) depending on acid strength and reaction conditions.

For example, treatment of the compound of formula (VII) in which X is chlorine with dilute HCl (1.0M) at 60° C. for 24 hours or with 2 M HCl under reflux for 1.5 hours, will yield the compound of formula (A). Treatment of the same compound of formula (VII) with 2 M HCl in tetrahydrofuran at room temperature will yield the compound of formula (I) in which X is chlorine.

If desired, the compound of formula (VII) in which X is chlorine may be converted to the compound of formula (VII) in which X is amino, prior to acid hydrolysis.

The conversion may be achieved by treatment with sodium azide in dimethylformamide to form an azido intermediate in which X is replaced by an azide moiety, followed by reduction of the intermediate with ammonium formate/palladium-on-charcoal in methanol.

The intermediate compound of formula (VII) in which X is chlorine and $R^c$ is hydrogen may be prepared by treating a compound of formula (VIII).

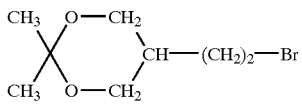

(VIII)

with a compound of formula (IX)

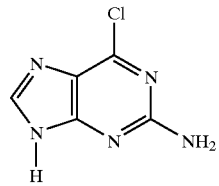

(IX)

The reaction may be carried out in an inert organic solvent, preferably dimethylformamide, in the presence of an inorganic base, preferably potassium carbonate.

The compound of formula (VIII) may itself be prepared by brominating a compound of formula (X)

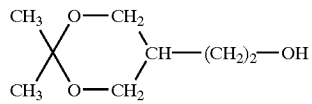

(X)

The reaction is preferably carried out by treating the compound of formula (X) with carbon tetrabromide and triphenylphosphine in an organic, aprotic solvent such as dimethylformamide.

The compound of formula (X) may itself be prepared by treating a compound of formula (XI)

$$HO-CH_2 \atop HO-CH_2 \!\!\!\!\!\!\!\!\!\!\!\!\!\!> CH-(CH_2)_2-OH$$

(XI)

with 2,2-dimethoxypropane and p-toluenesulphonic acid in the presence of acetone or tetrahydrofuran.

The compounds of formulae (IX) and (XI) are known compounds or can be prepared from known compounds by known methods.

The compounds of formulae (VII), (VIII) and (X) are novel intermediates and as such form further aspects of the present invention.

A compound of formula (I) or pharmaceutically acceptable salt, phosphate ester or acyl derivative thereof may be formulated for use in a pharmaceutical composition. Accordingly, in a further aspect of the invention, there is provided a pharmaceutical composition which comprises a compound of formula (I) or pharmaceutically acceptable salt, phosphate ester or acyl derivative thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that the patient may administer to himself a single dose. A suitable dosage unit might contain from 50 mg to 1 g of active ingredient, for example 100 to 500 mg. Such doses may administered 1 to 4 times a day or more usually 2 or 3 times a day. The effective dose of compound will in general be in the range of from 1.0 to 20 mg/kg of body weight per day or more usually 2.0 to 10 mg/kg per day.

In a further aspect of the invention there is provided a method of treating viral infections in a human or non-human animal, which comprises administering to the animal an effective, non-toxic amount of a compound of formula (I) or a pharmaceutically acceptable salt, phosphate ester or acyl derivative thereof.

The preparation of compounds of the invention is illustrated by the following Examples.

EXAMPLE 1

5-(2-Hydroxyethyl)-2,2-dimethyl-1,3-dioxan

To a suspension of lithium aluminium hydride (2.87 g, 76 mmol) in tetrahydrofuran (125 ml), a solution of triethyl 1,1,2-ethanetricarboxylate (9.2 ml, 9.85 g, 40 mmol) in tetrahydrofuran (25 ml) was added dropwise with stirring over 2 hours. Excess reagent was then quenched with aqueous tetrahydrofuran (1:2). The inorganic salts were filtered off and washed with ethanol (100 ml). The filtrate and washings were combined and the solvent was evaporated to afford a colourless oil (4.85 g). To a suspension of this oil in acetone (100 ml), 2,2-dimethoxypropane (25 ml) and p-toluenesulphonic acid monohydrate (2.3 g, 12 mmol) were added and the mixture was stirred for 1 hour. The resulting solution was neutralised with Amberlite IR 45 (OH⁻ form, methanol washed), filtered and the solvent evaporated under reduced pressure. The residue was purified by column chromatography on silica gel, eluting with chloroform-methanol mixtures (40:1 and 25:1) to afford 5-(2-hydroxyethyl)-2,2-dimethyl-1,3-dioxan as a colourless liquid (3.01 g, 47%); vmax (film) 3420, 2940, 1375, 1200 and 1080 cm$^{-1}$; $\delta_H$ (CDCl$_3$) 1.34–1.70 (8H, m, C(CH$_3$)$_2$ and C$\underline{H}_2$CH$_2$OH), 1.7–2.1 (1H, m, CH), 2.15 (1H, br, D$_2$O exchangeable, OH), and 3.5–4.0 (6H, m, 3×CH$_2$O); (Found: C, 58.33; H, 10.11%. C$_8$H$_{16}$O$_3$ 0.25H$_2$O requires C, 58.34; H, 10.10%. [M–CH$_3$]$^+$ found 145.0864; C$_7$H$_{13}$O$_3$ requires 145.0865).

Alternative Procedure for Preparation of 5-(2-Hydroxyethyl)-2,2-dimethyl-1,3-dioxan (Example 1)

A. 1,4-Dihydroxy-2-hydroxymethylbutane

To a refluxing solution of triethyl 1,1,2-ethanetricarboxylate (46 ml, 200 mmol) and sodium borohydride (20 g, 530 mmol) in t-butanol (400 ml), methanol was added in 3 aliquots over 30 minutes (total 25 ml). The solution was refluxed for a further 30 minutes and allowed to cool. Hydrochloric acid (5M) was carefully added to neutralise the solution. The solution was filtered and the inorganic residue was extracted with ethanol (2×100 ml) and filtered. The organic solutions were combined and the solvent removed. The residue was extracted with ethanol (120 ml) and the solution filtered. The solvent was removed to afford 1,4-dihydroxy-2-hydroxymethylbutane (24 g, 100%): $\delta_H$ (D$_2$O) 1.53 (2H, q, J 6 Hz, 3-H), 1.75 (1H, m, 2-H), 3.57 (4H, d, J 6 Hz, 1-H and 1'-H), and 3.64 (2H, t, J 6 Hz, 4-H).

B. 5-(2-Hydroxyethyl)-2,2-dimethyl-1,3-dioxan

To a solution of 1,4-dihydroxy-2-hydroxymethylbutane (12 g, 100 mmol) in tetrahydrofuran (25 ml), 2,2-dimethoxypropane (13.5 g, 110 mmol) and p-toluenesulphonic acid monohydrate (0.57 g, 3 mmol) were added. The solution was stirred for 0.5 hour at room temperature and was then neutralised by addition of triethylamine. The solvent was removed and the residue purified by column chromatography on silica gel eluting with chloroform-methanol mixtures to afford 5-(2-hydroxyethyl)-2,2-dimethyl-1,3-dioxan as a clear colourless liquid (6.5 g, 41%).

EXAMPLE 2

5-(2-Bromoethyl)-2,2-dimethyl-1,3-dioxan

To an ice-cooled solution of 5-(2-hydroxyethyl)-2,2-dimethyl-1,3-dioxan (1.92 g, 12 mmol) and carbon tetrabromide (7.96 g, 24 mmol) in dimethylformamide (100 ml), triphenylphosphine (6.30 g, 24 mmol) was added and the solution was left at 4° C. overnight. To this solution methanol (20 ml) was added and the solvent was then evaporated under reduced pressure. The residue was purified by column chromatography on silica gel, elutingwith hexane-acetone (12:1) to afford 5-(2-bromoethyl)-2,2-dimethyl-1,3-dioxan as a clear colourless liquid (0.89 g, 40%); vmax (film) 2940, 1370, 1270, 1260, 1200, and 1070 cm$^{-1}$; $\delta_H$ (CDCl$_3$) 1.42 (6H, s, C(CH$_3$)$_2$), 1.94 (3H, m, C$\underline{H}$CH$_2$CH$_2$Br), 3.43 (2H, t, J 7 Hz, CH$_2$Br), and 3.5–4.1 (4H, m, 2×CH$_2$O); (Found: C, 42.84; H, 6.93%. C$_8$H$_{15}$BrO$_2$ requires: C, 43.07; H, 6.78%. [M–CH$_3$] found 207.0024; C$_7$H$_{12}$BrO$_2$ requires 207.0021).

Alternative Procedure for Preparation of 5-(2-Bromoethyl)-2,2-dimethyl-1-3-dioxan (Example 2)

To an ice-cooled solution of 5-(2-hydroxyethyl)-2,2-dimethyl-1,3-dioxan (6.08 g, 38 mmol) and carbon tetrabromide (18.90 g, 57 mmol) in N,N-dimethylformamide (110 ml); triphenylphosphine (14.95 g, 57 mmol) was added. The solution was stirred for 0.5 hour at 0° C. The solution was then diluted with saturated aqueous sodium bicarbonate (55 ml) followed by water (55 ml), and was extracted with hexane (2×150 ml). The combined organic layers were dried (magnesium sulphate) and the solvent removed. The residue was placed under high vacuum for 2 hours to remove bromoform. The residue was taken up in a small amount of hexane, filtered and the solvent removed to afford 5-(2-bromoethyl)-2,2-dimethyl-1,3-dioxan (7.40 g, 87%) as a colourless oil which crystallised on cooling, m.p. ca. 18° C.

EXAMPLE 3

2-Amino-6-chloro-9-[2-(2,2-dimethyl-1,3-dioxan-5-yl)ethyl]-purine

To a solution of 5-(2-bromoethyl)-2,2-dimethyl-1,3-dioxan (0.75 g, 3.7 mmol) in dry dimethylformamide (12 ml) 2-amino-6-chloropurine (0.68 g, 4.0 mmol) and then anhydrous potassium carbonate (0.83, 6.0 mmol) were added. The solution was stirred at room temperature for 5 hours and left at 4° C. overnight. The solution was filtered and the solvent removed. The residue was purified by column chromatography on silica gel, eluting with chloroform-methanol mixtures (80:1 and 60:1) to afford 2-amino-6-chloro-9-[2-(2,2-dimethyl-1,3-dioxan-5-yl) ethyl]purine as a white crystalline solid (0.74 g, 64%), m.p. 125–126°C.; λmax (H$_2$O) 223 (ε 28,900), 247 (ε 5,700), and 310 (ε 7,700) nm; νmax (KBr) 3450, 3340, 1635, 1615, 1565, 1470, 1410, and 1375 cm$^{-1}$; δ$_H$ [(CD$_3$)$_2$SO]1.26 (3H, s, CH$_3$), 1.32 (3H, s, CH$_3$), 1.45–1.85 (3H, m, CHCH$_2$CH$_2$N), 3.51 (2H, dd, J 11 Hz and J 7 Hz, 2×H$_{ax}$) 3.78 (2H, dd, J 11 Hz and J 4 Hz, 2×H$_{eq}$), 4.05 (2H, t, J 7 Hz, CH$_2$N), 6.89 (2H, s, D$_2$O exchangeable, 2-NH$_2$), and 8.38 (1H, s, 8-H); (Found: C, 50.37; H, 5.68; N, 22.22%; M$^+$ 311.1136. C$_{13}$H$_{18}$ClN$_5$O$_2$ requires C, 50.08; H, 5.82; N, 22.46%; M$^+$ 311.1149).

EXAMPLE 4

9-(4-Hydroxy-3-hydroxymethylbut-1-yl)guanine

2-Amino-6-chloro-9-[2-(2,2-dimethyl-1,3-dioxan-5-yl) ethyl]purine (0.59 g, 1.9 mmol) in hydrochloric acid (1.0M, 4 ml) was stirred at 60° C. for 24 hours. The solution was diluted with water and neutralised with Amberlite IR 45 (OH$^-$ form). The mixture was filtered, the resin washed with water and the solvent evaporated under reduced pressure. The residue was recrystallised from water to afford 9-(4-hydroxy-3-hydroxymethylbut-1-yl)guanine (238 mg, 49%), m.p. 275–277° C.; λmax (H$_2$O) 253 (ε 11,500) and 270 (shoulder, ε 8,630) nm; νmax (KBr) 3420, 3140, 1690, 1645, and 1605 cm$^{-1}$; δ$_H$ [(CD$_3$)$_2$SO] 1.3–1.5 (3H, m, CHCH$_2$CH$_2$), 3.42 (4H, d, J 5 Hz, 2×CH$_2$O), 3.99 (2H, t, J 7 Hz, CH$_2$N), 4.41 (2H, br, D$_2$O exchangeable, 2×OH), 6.44 (2H, s, D$_2$O exchangeable, 2-NH$_2$), 7.71 (1H, s, 8-H), and 10.55 (1H, br, D$_2$O exchangeable, 1-H); (M$^+$ found 253.1176. C$_{10}$H$_{15}$N$_5$O$_3$ requires M$^+$ 253.1175).

Alternative Procedure for Preparation of 9-(4-Hydroxy-3-hydroxymethylbut-1-yl)quanine (Example 4)

2-Amino-6-chloro-9-[2-(2,2-dimethyl-1,3-dioxan-5-yl) ethyl]purine (3.74 g, 12 mmol) in hydrochloric acid (2.0M, 12 ml) was heated under reflux for 1.5 hours. The solution was neutralised with aqueous sodium hydroxide (10%) and then allowed to cool. The solution was filtered and the solid washed with water to afford 9-(4-hydroxy-3-hydroxymethylbut-1-yl)guanine as a white crystalline solid (2.18 g, 72%), m.p. 275–277° C.; (Found: C, 47.31; H, 6.02; N, 27.81%; C$_{10}$H$_{15}$N$_5$O$_3$ requires C, 47.43; H, 5.97; N, 27.65%).

EXAMPLE 5

Ethyl 4-benzyloxy-2-ethoxycarbonylbutanoate

Sodium metal (72 g, 3.13 mmol) was dissolved in dry ethanol (1.21) with stirring, then diethyl malonate (477 ml, 3.13 mmol) and potassium iodide (249.5 g, 1.5 mmol) were added. An oil containing benzyl-2-bromoethyl ether (278.5 g, 1.3 mmol) contaminated with ethylene carbonate (198 g) was then added slowly to the stirred mixture. On completion of the addition, the reaction mixture was heated under reflux for 18 hours, then poured into ice-water (7.51) and extracted with ether (3×1.61). The ether fractions were combined, dried (MgSO$_4$), filtered and evaporated to give an oil (550 g). This was vacuum distilled to give ethyl 4-benzyloxy-2-ethoxycarbonyl-butanoate (313 g, 82%) as a clear oil, b.p. 165–180°/2 mm. δ$_H$ (CDCl$_3$) 1.22 (6H, t, 2×CH$_3$), 2.18 (2H, q, CHCH$_2$), 3.48 (2H, t, CHCH$_2$O), 3.55 (1H, t, CH), 4.12 (4H, q, 2×CO$_2$CH$_2$), 4.38 (2H, s, OCH$_2$Ph), 7.21 (5H, s, Ar).

EXAMPLE 6

4-Benzyloxy-2-hydroxymethylbutan-1-ol

To a cooled, stirred suspension of lithium aluminium hydride (103 g, 2.7 mol) in dry ether (2.51) under nitrogen was added ethyl 4-benzyloxy-2-ethoxycarbonyl-butanoate (362 g, 1.23 mol) over a period of 3 hours. On completion of the addition, the reaction mixture was allowed to warm to room temperature, and then heated under reflux for 1 hour. It was then re-cooled and the excess lithium aluminium hydride destroyed by dropwise addition of water (100 ml), 2M sodium hydroxide (100 ml) and water (300 ml). The reaction mixture was filtered, and the filter cake washed well with chloroform. The filtrate was dried (MgSO$_4$), filtered, and evaporated to give 4-benzyloxy-2-hydroxymethylbutan-1-ol as a clear oil (226 g, 87%). δ$_H$ (CDCl$_3$) 1.35–2.05 (3H, m, CHCH$_2$CH$_2$), 3.30–3.80 (8H, m, 3×CH$_2$O, 2×OH), 4.42 (2H, s, OCH$_2$Ph) 7.26 (5H, s, Ar).

EXAMPLE 7

2-Acetoxymethyl-4-benzyloxybut-1-yl acetate

To a cooled solution of 4-benzyloxy-2-hydroxymethylbutan-1-ol in dry pyridine (1.1 l) was added acetyl chloride (230 ml, 3.24 mol) over 2 hours, the temperature being maintained below 8° C. On completion of the addition, the reaction mixture was stirred at 5° C. for a further 1 hour, then poured into water (41) and extracted with ethyl acetate (1×31, 1×21). The organic extracts were combined and washed with 2M hydrochloric acid (2×1 l), water (1 l) and brine (1 l), dried (MgSO$_4$), filtered and evaporated to give a pale yellow oil (300 g).

Vacuum distillation afforded 2-acetoxymethyl-4-benzyloxybut-1-yl acetate as a colourless oil (220 g, 70%) b.p. 160–165°/0.05 mm.

The fraction b.p. 122–160°/0.05 mm (42 g) was purified by column chromatography on silica gel, elution with ether-hexane 2:3 affording further 2-acetoxymethyl-4-benzyloxybut-1-yl acetate (27 g, 8%). δ$_H$ (CDCl$_3$) 1.68 (2H, q, CHCH$_2$CH$_2$), 2.01 (6H, s, 2×OCOCH$_3$), 2.19 (1H, m, CH), 3.50 (2H, t, CH$_2$OCH$_2$Ph), 4.03 (4H, d, CH$_2$OCOCH$_3$), 4.43 (2H, s, OCH$_2$Ph), 7.24 (5H, s, Ar).

EXAMPLE 8

2-Acetoxymethyl-4-hydroxybut-1-yl acetate

To a solution of 2-acetoxymethyl-4-benzyloxy-but-1-yl acetate (55 g, 0.187 mol) in ethanol (250 ml) was added 10% palladium on carbon (2.5 g), and the mixture hydrogenated at atmospheric pressure and room temperature. When the theoretical hydrogen uptake had been achieved (18 hours), the reaction was stopped and filtered through Celite. Evaporation of the filtrate gave a colourless oil (35 g). This was purified by column chromatography on silica gel, elution with 2% methanol in chloroform affording 2-acetoxymethyl-4-hydroxybut-1-yl acetate as a clear oil (32.9, 86%). δ$_H$ (CDCl$_3$) 1.61 (2H, q, CHCH$_2$CH$_2$), 2.04 (6H, s, 2×OCOCH$_3$), 2.20 (1H, m, CH), 2.61 (1H, br s, D$_2$O exchangeable, OH), 3.68 (2H, t, CH$_2$OH), 4.04 (4H, d, 2×CH$_2$OCOCH$_3$).

EXAMPLE 9

Acetoxymethyl-4-bromobut-1-yl acetate

A mixture of 2-acetoxymethyl-4-hydroxy-but-1-yl acetate (10 g, 49 mmol), triphenyl phosphine (19.25 g, 73 mmol) and carbon tetrabromide (24.4 g, 73 mmol) was stirred for 18 hours at 4° C. in dimethylformamide (150 ml). The solvent was then evaporated, and the residue purified by column chromatography on silica gel, eluting with ether-light petroleum 2:3 to afford 2-acetoxymethyl-4-bromobut-1-yl acetate as a pale oil (130 g, 99%). $\delta_H$ (CDCl$_3$) 1.73–2.56 (3H, m, CHCH$_2$CH$_2$), 2.04 (6H, s, 2×OCOCH$_3$), 3.44 (2H, t, CH$_2$Br), 4.04 (4H, d, 2×CH$_2$OCOCH$_3$).

EXAMPLES 11 AND 10

9-(4-Acetoxy-3-acetoxymethylbut-1-yl)-2-amino-6-chloropurine and 7-(4-Acetoxy-3-acetoxymethylbut-1-yl)-2-amino-6-chloropurine A mixture of 2-acetoxymethyl-4-bromobut-1-yl-acetate (13.0 g, 48.7 mmol), 2-amino-6-chloro-purine (8.25g, 48.7 mmol) and anhydrous potassium carbonate (10 g, 72.5 mmol) was stirred in dry dimethylformamide (100 ml) for 18 hours at room temperature. The reaction mixture was then filtered, the filtrate evaporated, and the residue purified by column chromatography on silica gel (500 g). Elution with 3% methanol in chloroform afforded 9-(4-acetoxy-3-acetoxymethyl-but-1-yl)-2-amino-6-chloropurine as a white solid (13.8 g, 80%) mp 135–137°. $\lambda_{max}$ (H$_2$O) 222 ($\epsilon$ 28,500), 245 ($\epsilon$ 4,800) 307 ($\epsilon$ 7,700) nm; $\nu_{max}$ (KBr) 3485, 3310, 3200, 1750, 1730, 1625, 1560, 1525, 1475, 1245 cm$^{-1}$. $\delta_H$ [(CD$_3$)$_2$SO] (270 MHz) 1.85–2.05 (3H, m, CHCH$_2$CH$_2$), 2.01 (6H, s, 2×OCOCH$_3$), 4.03 (4H, d, 2×CH$_2$OCOCH$_3$) 4.16 (2H, t, CH$_2$N), 6.88 (2H, br s, D$_2$O exchangeable, NH$_2$), 8.17 (1H, s, 8-H). Found C, 47.27; H, 4.94; N, 19.56%. C$_{14}$H$_{18}$N$_5$O$_4$Cl requires C, 47.26; H, 5.10; N 19.68%.

Subsequent elution wizh 5% methanol in chloroform afforded 7-(4-acetoxy-3-acetoxymethylbut-1-yl)-2-amino-6-chloropurine as a white solid (2.9 g, 17%) mp 174–175° (dec). $\lambda_{max}$ (H$_2$O) 222 ($\epsilon$ 25,000), 255 ($\epsilon$ 3,900), 318 ($\epsilon$ 5,600) nm; $\nu_{max}$ (KBr) 3390, 3310, 3205, 1745, 1735, 1635, 1550, 1505, 1380, 1365, 1310, 1250, 1240 cm$^{-1}$. $\delta_H$ [(CD$_3$)$_2$SO] (270 MHz) 1.86 (2H, q, CHCH$_2$CH$_2$), 1.99 (6H, s, 2×OCOCH$_3$), 1.95–2.05 (1H, m, CH), 4.03 (4H, d, 2×CH$_2$OCOCH$_3$), 4.38 (2H, t, CH$_2$N), 6.60 (2H, br s, D$_2$O exchangeable, NH$_2$), 8.39 (1H, s, 8-H). Found C, 47.48; H, 5.11; N, 19.52%. C$_{14}$H$_{18}$N$_5$O$_4$Cl requires C, 47.26; H, 5.10; N, 19.68%.

Alternative Procedure for Preparation of 9-(4-Hydroxy-3-hydroxymethylbut-1-yl)guanine (Example 4)

A solution of 9-(4-acetoxy-3-acetoxymethyl-but-1-yl)-2-amino-6-chloropurine (15.5 g, 43.6 mmol) in 2M hydrochloric acid (150 ml) was heated under reflux for 2 hours. The solution was then cooled to room temperature and neutralised with 10% sodium hydroxide solution, left to stand at 4° C., and the resulting precipitate filtered off, washed with cold water and recrystallized from water to give 9-(4-hydroxy-3-hydroxymethylbut-1-yl)guanine as a white crystalline solid (9.4 g, 85%) mp 275–277°.

EXAMPLE 12

9-(4-Hydroxy-3-hydroxymethylbut-1-yl)guanine, sodium salt

To a suspension of 9-(4-hydroxy-3-hydroxymethylbut-1-yl)-guanine (0.30 g, 1.2 mmol) in water (8 ml) was added aqueous sodium hydroxide (1M, 1.2 ml). The solvent was removed from the resulting clear solution and trituration with methanol-ethanol afforded 9-(4-hydroxy-3-hydroxymethylbut-1-yl)guanine sodium salt as a white solid (0.32 g, 97%); $\lambda$max (H$_2$O, pH7.8) 252 (11,300) nm; $\nu$max (KBr) 3400, 1590, and 1570 cm$^{-1}$; $\delta_H$ [(CD$_3$)$_2$SO] 1.47 (1H, m, 3'-H), 1.70 (2H, q, J 7 Hz, 2'-H), 3.3–3.5 (4H, AB part of ABX, 2×4'-H), 3.96 (2H, t, J 7 Hz, 1'-H), 4.7 (2H, br, D$_2$O exchangeable, 2×OH), 5.58 (2H, br.s, D$_2$O exchangeable, 2-NH$_2$), and 7.43 (1H, s, 8-H).

EXAMPLE 13

9-(4-Hydroxy-3-hydroxymethylbut-1-yl)guanine, Potassium Salt

To a suspension of 9-(4-hydroxy-3-hydroxymethylbut-1-yl)guanine (0.30 g, 1.2 mmol) in water (8 ml) was added aqueous potassium hydroxide (1M, 1.2 ml). The solvent was removed from the resulting clear solution and trituration with methanol-ethanol afforded 9-(4-hydroxy-3-hydroxymethylbut-1-yl)guanine potassium salt as a white powdery solid (0.34 g, 97%); $\lambda$max (H$_2$O, pH7.4) 252 (12,400); $\nu$max (KBr) 3360, 3180, 1690, 1650, 1585, 1570, and 1480 cm$^{-1}$; $\delta_H$ [(CD$_3$)$_2$SO] 1.47 (1H, m, 3'-H), 1.69 (2H, q, J 7.1 Hz, 2'-H), 3.3–3.5 (4H, AB part of ABX, 2×4'-H), 3.94 (2H, t, J 7.3 Hz, 1'-H), 4.7 (2H, br, D$_2$O exchangeable, 2×OH), 5.69 (2H, br.s, D$_2$O exchangeable, 2-NH$_2$), and 7.38 (1H, s, 8-H); (Found: C, 41.11; H, 4.91; N, 23.82%; C$_{10}$H$_{14}$N$_5$O$_3$K requires: C, 41.22; J, 4.84; N, 24.04%).

EXAMPLE 14

2-Amino-6-chloro-9-(4-hydroxy-3-hydroxymethylbut-1-yl)purine hydrochloride

To a solution of 2-amino-6-chloro-9-[2-(2,2-dimethyl-1,3-dioxan-5-yl)ethyl]purine (0.46 g, 1.5 mmol) in tetrahydrofuran (4.5 ml), hydrochloric acid (2.0M, 0.5 ml) was added. A white precipitate formed and after 0.5 hour the solution was diluted with further tetrahydrofuran and was filtered to give 2-amino-6-chloro-9-(4-hydroxy-3-hydroxymethylbut-1-yl) purine hydrochloride (290 mg, 63%), decomposed over 165° C.; $\lambda$max (H$_2$O, pH5.5) 223 ($\epsilon$ 28,400), 245 ($\epsilon$ 4,620), and 307 ($\epsilon$ 7,620) nm; $\nu$max (KBr) 3370, 3330, 3200, 2500, 1650, 1630, 1595, and 1505 cm$^{-1}$; $\delta_H$ [(CD$_3$)$_2$SO] 1.53 (1H, m, CHCH$_2$CH$_2$), 1.83 (2H, q, J 7 Hz, CHCH$_2$CH$_2$), 3.35 (4H, d, J 6 Hz, 2×CH$_2$O), 4.19 (2H, t, J 7 Hz, CH$_2$N), 5.85 (9H, s, D$_2$O exchangeable, 2×OH, NH$_2$, HCl and H$_2$O), and 8.57 (1H, s, 8-H). (Found: C, 39.04; H, 4.85; N. 22.36%; C$_{10}$H$_{14}$ClN$_5$O$_4$.HCl requires C, 38.98; H, 4.91; N, 22.73%).

EXAMPLE 15

2-Aniino-9-(4-hydroxy-3-hydroxymethylbut-1-yl)-6-methoxypurine

To a solution of 2-amino-6-chloro-9-[2-(2,2-dimethyl-1,3-dioxan-5-yl)ethyl]purine (0.28 g, 0.9 mmol) in methanol (2.5 ml), methanolic sodium methoxide (1M, 1.0 ml) was added and the solution was stirred at 50° for 1.5 hours. The solution was allowed to cool and hydrochloric acid (5M, 0.2 ml) and water (0.4 ml) were added. After 15 minutes the solution was neutralised with 10% aqueous sodium hydroxide. Silica gel was added and the solvent removed. Column chromatography on silica gel eluting with chloroform-methanol mixtures afforded 2-amino-9-(4-hydroxy-3- hydroxymethylbut-1-yl)-6-methoxypurine (185 mg, 77%), m.p. 117–119° C.; λmax (H$_2$O) 213 (ε 22,100), 249 (ε 6,860), and 280 (ε 8,410) nm; νmax (KBr) 3400, 3240, 3210, 1640, 1610, 1590, 1410, and 1395 cm$^{-1}$; δ$_H$ [(CD$_3$)$_2$SO] 1.47 (1H, m, CHCH$_2$CH$_2$), 1.74 (2H, q, J 7 Hz, CHCH$_2$CH$_2$), 3.40 (4H, d, J 6 Hz, 2×CH$_2$O), 3.95 (3H, s, OCH$_3$), 4.06 (2H, t, J 7 Hz, CH$_2$N), 4.4 (2H, br, D$_2$O exchangeable, 2×OH), 6.33 (2H, s, D$_2$O exchangeable, 2-NH$_2$), and 7.46 (1H, s, 8-H) (Found: M$^+$ 267.1340; C$_{11}$H$_{17}$N$_5$O$_3$ requires M$^+$ 267.1331).

EXAMPLE 16

2-Amino-6-ethoxy-9-(4-hydroxy-3-hydroxymethylbut-1-yl)purine

To a suspension of 2-amino-6-chloro-9-(2-[2,2-dimethyl-1,3-dioxan-5-yl)ethyl]purine (0.31 g, 1.0 mmol) in ethanol (1.5 ml) was added sodium ethoxide (1M in ethanol, 1.5 ml) and the mixture was stirred at 60° for 1 hour. The resulting solution was allowed to cool, hydrochloric acid (5M, 0.3 ml) and water (0.7 ml) were added and the solution was stirred for 1 hour at room temperature. The solution was neutralised by addition of aqueous sodium bicarbonate and the solvent was removed. The residue was extracted with chloroform-ethanol (2:1), the solution was filtered and the solvent removed. The residue was purified by column chromatography on silica gel eluting with chlorororm-methanol (6:1) to afford 2-amino-6-ethoxy-9-(4-hydroxy-3-hydroxymethylbut-1-yl)purine (0.24 g, 85%), m.p. 150–152° C.; λmax (H$_2$O) 213 (24,3000), 249 (7,360), and 280 (9,270) nm; νmax (KBr) 3330, 3210, 2900, 1650, 1610, 1580 cm$^{-1}$; δ$_H$ [(CD$_3$)$_2$SO] 1.3–1.6 (4H, m, 3'-H and CH$_3$), 1.73 (2H, q, J 7 Hz, 2'-H), 3.2–3.6 (4H, AB part of ABX, 2×4'-H) 4.04 (2H, t, J 7 Hz, 1'-H), 4.3–4.55 (4H, m, 2H D$_2$O exchangeable, 2×OH; D$_2$O exchange leaves 2H, q, J 7 Hz, 6-OCH$_2$), 6.30 (2H, s, D$_2$O exchangeable, 2-NH$_2$), and 7.84 (1H, s, 8-H); (Found: C, 50.91; H, 7.00; N, 24.89%; C$_{12}$H$_{19}$N$_5$O$_3$ requires C, 51.23; H, 6.81; N, 24.90%).

EXAMPLE 17

2-Amino-6-benzyloxy-9-(4-hydroxy-3-hydroxymethylbut-1-yl)purine

A suspension of 2-amino-6-chloro-9-[2-(2,2-dimethyl-1,3-dioxan-5-yl)ethyl]purine (0.31 g, 1.0 mmol) in a solution of sodium benzoxide (1M in benzyl alcohol, 2 ml) was stirred at 70° for 1 hour. The resulting solution was allowed to cool, hydrochloric acid (5M, 0.4 ml) and water (0.6 ml) were added and the solution was stirred for 1 hour at room temperature. The solution was then partitioned between chloroform and water. The aqueous layer was neutralised with aqueous sodium bicarbonate and extracted with chloroform. The combined organic layers were washed with aqueous sodium bicarbonate, dried (magnesium sulphate) and the solvent was removed. The residue was purified by column chromatography on silica gel eluting with chloroform-methanol mixtures (10:1, 5:1) to afford 2-amino-6-benzyloxy-9-(4-hydroxy-3-hydroxymethylbut-1-yl)purine as a white crystalline solid (0.17 g, 50%), m.p. 146–147.5° C.; λmax (EtOH) 212 (32,300), 250 (8,380), and 283 (10,100) nm; νmax (KBr) 3340, 3220, 1655, 1605, and 1580 cm$^{-1}$; δ$_H$ [(CD$_3$)$_2$SO] 1.3–1.6 (1H, m, 3'-H), 1.72 (2H, q, J 7 Hz, 2'-H), 3.38 (4H, AB part of ABX, 2×4'-H), 4.03 (2H, t, J 7 Hz, 1'-H), 4.36 (2H, t, J 5.5 Hz, D$_2$O exchangeable, 2×OH), 5.47 (2H, s, PhCH$_2$), 6.37 (2H, s, D$_2$O exchangeable, 2-NH$_2$), 7.3–7.6 (5H, m, C$_6$H$_5$), and 7.84 (1H, s, 8-H); (Found: C, 58.89; H, 6.12; N, 19.87%; C$_{17}$H$_{21}$N$_5$O$_3$ requires C, 59.46; H, 6.16; N, 20.40%).

EXAMPLE 18

2-Amino-9-(4-hydroxy-3-hydroxymethylbut-1-yl)-6-thiopurine

A solution of 2-amino-6-chloro-9-[2-(2,2-dimethyl-1,3-dioxan-5-yl)ethyl]purine (0.31 g, 1.0 mmol) in aqueous sodium hydrosulphide (2M, 3.0 ml) and ethanol (1.5 ml) was stirred at 70° C. for 1 hour. To this solution glacial acetic acid (2.5 ml) was added and the mixture was stirred for further 1 hour at 70° C. The solution was allowed to cool, filtered and the solvent removed. The residue was recrystallised from water to afford 2-amino-9-(4-hydroxy-3-hydroxymethylbut-1-yl)-6-thiopurine (0.13 g, 48%), m.p. decomposed at 260° C.; δ$_H$ [(CD$_3$)$_2$SO] 1.45 (1H, m, CHCH$_2$CH$_2$), 1.72 (2H, q, J 7 Hz, CHCH$_2$CH$_2$), 3.3–3.5 (4H, ABX J$_{AB}$ 10.7 Hz, J$_{AX}$ 5.5 Hz and J$_{BX}$ 5.8 Hz, 2×CH$_2$O), 4.02 (2H, t, J 7.4 Hz, CH$_2$N), 4.45 (2H, br, D$_2$O exchangeable, 2×OH), 6.77 (2H, s, D$_2$O exchangeable, 2-NH$_2$), 7.87 (1H, s, 8-H), and 11.9 (1H, br, D$_2$O exchangeable, 1-H); λmax (H$_2$O) 230 (ε 16,900), 263 (ε 7,210) and 341 (ε 25,200) nm; νmax (KBr) 3310, 3130, 1650, 1610, and 1580 cm$^{-1}$; (Found: C, 44.86; H, 5.60; N, 25.44%; C$_{10}$H$_{15}$N$_5$O$_2$S requires C, 44.60; H, 5.61; N, 26.00%).

EXAMPLE 19

2-Amino-6-azido-9-[2-(2,2-dimethyl-1,3-dioxan-5-yl)ethyl]purine

To a solution of 2-amino-6-chloro-9-[2-(2,2-dimethyl-1,3-dioxan-5-yl)ethyl]purine (0.47 g, 1.5 mmol) in dry N,N-dimethylformamide (5 ml), sodium azide (0.20 g, 3.0 mmol) was added and the mixture was stirred at 100–110° C. for 4 hours. The solvent was removed and the residue washed with water to leave 2-amino-6-azido-9-[2-(2,2-dimethyl-1,3-dioxan-5-yl)ethyl]purine as a crystalline solid (0.36 g, 75%), m.p. decomposed at 200° C.; λmax (MeOH) 272 (ε 8,210) and 301 (ε 10,100) nm; νmax (KBr) 1670, 1625, and 1560 cm$^{-1}$; δ$_H$ (CDCl$_3$-CD$_3$OD) 1.44 (6H, s, C(CH$_3$)$_2$), 1.6–2.2 (3H, m, CH$_2$CHCH$_2$), 3.5–3.8 (2H, dd (ABX), J 7 Hz and J 11 Hz, 2×H$_{ax}$), 3.85–4.15 (2H, dd (ABX), J 4 Hz and J 11 Hz, 2×H$_{eq}$), 4.29 (2H, t, J 7 Hz, CH$_2$N), and 7.93 (1H, s, 8-H) (Found: C, 48.96; H, 5.66; N, 35.15%; M$^+$ 318.1553. C$_{13}$H$_{18}$N$_8$O$_2$ requires C, 49.05; H, 5.70; N, 35.20%; M$^+$ 318.1546).

EXAMPLE 20

2,6-Diamino-9-[2-(2,2-dimethyl-1,3-dioxan-5-yl)ethyl]purine

A mixture of 2-amino-6-azido-9-[2-(2,2-dimethyl-1,3-dioxan-5-yl)ethyl]purine (318 mg, 1.0 mmol), formic acid (0.15 ml, 4.0 mmol), concentrated ammonia (0.22 ml, 4.0 mmol), 10% palladium-on-charcoal (30 mg) and methanol (10 ml) was heated under reflux for 1 hour. The solution was allowed to cool, filtered and the solvent removed. The residue was purified by column chromatography on silica gel eluting with chloroform-methanol mixtures (20:1 and 15:1) to give 2,6-diamino-9-[2-(2,2-dimethyl-1,3-dioxan-5-yl)ethyl]purine (190 mg, 65%), m.p. 202–204° C.); νmax (KBr) 1670, 1640, 1595, and 1410 cm$^{-1}$; δ$_H$ (CDCl$_3$-CD$_3$OD) 1.42 (6H, s, C(CH$_2$)$_2$), 1.6–2.0 (3H, m, CHCH$_2$CH$_2$), 3.5–4.2 (6H, m, 2×CH$_2$O and CH$_2$N), and 7.68 (1H, s, 8-H) (Found: C, 52.88; H, 6.78; N, 28.36%; M$^+$ 292.1652. C$_{13}$H$_{20}$N$_6$O$_2$ requires C, 53.41; H, 6.90; N, 28.75%; M$^+$ 292.1648).

EXAMPLE 21

2,6-Diamino-9-(4-hydroxy-3-hydroxymethylbut-1-yl)purine

A solution of 2,6-diamino-9-[2-(2,2-dimethyl-1,3-dioxan-5-yl)ethyl]purine (180 mg, 0.6 mmol) in 70% acetic acid (10 ml) was stirred for 1 hour at room temperature. The solvent was removed, the residue was suspended in methanol and sodium methoxide was added to neutralise. Column chromatography on silica gel eluting with chloroform-methanol mixtures (6:1, 4:1 and 3:1) gave 2,6-diamino-9-(4-hydroxy-3-hydroxymethylbut-1-yl)purine (95 mg, 63%), m.p. 187–190° C.; λmax ($H_2O$, pH6.5) 215 (ε 25,500), 255 (ε 7,290), and 280 (ε 9,170) nm; vmax 3150, 1680, 1650, 1605, 1590, and 1410 $cm^{-1}$; $δ_H$ [$(CD_3)_2SO$] 1.46 (1H, m, CHCH$_2$CH$_2$), 1.73 (2H, q, J 7.1 Hz, CHCH$_2$CH$_2$), 3.3–3.5 (4H, ddd (ABX), $J_{AB}$ 10.6 Hz, $J_{AX}$ 5.5 Hz and $J_{BX}$ 5.9 Hz, 2×CH$_2$O), 4.01 (2H, t, J 7.3 Hz, CH$_2$N), 4.41 (2H, br, D$_2$O exchangeable, 2×OH), 5.70 (2H, s, D$_2$O exchangeable, NH$_2$), 6.56 (2H, s, D$_2$O exchangeable, NH$_2$), and 7.69 (1H, s, 8-H) (Found: C, 46.09; H, 6.32; N, 31.69%; $C_{10}H_{16}N_6O_2$·0.1CHCl$_3$ requires C, 45.91; H, 6.14; N, 31.81%).

EXAMPLE 22

9-(4-Acetoxy-3-acetoxymethylbut-1-yl)guanine

A mixture of 9-(4-hydroxy-3-hydroxymethylbut-1-yl)guanine (253 mg, 1.0 mmol), 4-dimethylaminopyridine (25 mg) and acetic anhydride (8.5 ml) was stirred for 4 days at room temperature. The acetic anhydride was removed under reduced pressure. The residue was purified by column chromatography on silica gel eluting with chloroform-methanol mixtures (20:1 and 10:1) to afford 9-(4-acetoxy-3-acetoxymethylbut-1-yl)guanine (160 mg, 47%) which was recrystallised from methanol, m.p. 202–205° C.; vmax (KBr) 1737, 1690, 1628, 1600, and 1240 $cm^{-1}$; $δ_H$[$(CD_3)_2SO$] 1.79 (2H, q, J 6.7 Hz, CHCH$_2$CH$_2$), 1.91 (1H, m, CHCH$_2$CH$_2$), 2.00 (6H, s, 2×CH$_3$), 4.00 (6H, m, 2×CH$_2$O and CH$_2$N), 6.42 (2H, s, D$_2$O exchangeable, 2-NH$_2$), 7.71 (1H, s, 8-H), and 10.54 (1H, s, D$_2$O exchangeable, 1-H); $δ_C$ [$(CD_3)_2SO$] 20.71 (2×CH$_3$), 23.29 (C-2'), 34.54 (C-3'), 40.59 (C-1'), 63.58 (2×C-4'), 116.64 (C-5), 137.58 (C-8), 151.24 (C-4), 153.38 (C-2), 156.87 (C-6), and 170.57 (2×COO) (Found: C, 49.62; H, 5.70; N, 20.51%; M$^+$ 337.1392; $C_{14}H_{19}N_5O_5$ requires C, 49.85; H, 5.68; N, 20.76%; M$^+$ 337.1386).

EXAMPLES 23 AND 24

9-(4-Propionyloxy-3-propionyloxymethylbut-1-yl)guanine (Example 23) and N$^2$-Propionyl-9-(4-propionyloxy-3-propionyloxymethylbut-1-yl)guanine (Example 24)

A mixture of 9-(4-hydroxy-3-hydroxymethylbut-1-yl)guanine (253 mg, 1.0 mmol), 4-dimethylaminopyridine (30 mg), propionic anhydride (8 ml) and N,N-dimethylformamide (15 ml) was stirred at room temperature for 66 hours. The solvent was removed and the residue subjected to column chromatography on silica gel eluting with chloroform-methanol mixtures (30:1, 20:1, 10:1). The first compound to elute was N$^2$-propionyl-9-(4-propionyloxy-3-propionyloxymethylbut-1-yl)guanine (200 mg, 47%) which was recrystallised from ether-methanol, m.p. 152–154° C.; vmax (KBr) 1740, 1675, 1610, 1560, and 1185 $cm^{-1}$; $δ_H$ (CDCl$_3$) 1.14 (6H, t, J 7.5 Hz, 2×OCOCH$_2$CH$_3$), 1.27 (3H, t, J 7.5 Hz, NCOCH$_2$CH$_3$), 1.88 (2H, q, J 6.9 Hz, CHCH$_2$CH$_2$), 2.01 (1H, m, CHCH$_2$CH$_2$), 2.35 (2H, q, J 7.5 Hz, 2×OCOCH$_2$CH$_3$), 2.56 (2H, q, J 7.5 Hz, NCOCH$_2$CH$_3$), 4.1–4.3 (6H, m, 2×CH$_2$O and CH$_2$N), 7.65 (1H, s, 8-H), 9.14 (1H, s, N—H), and 11.95 (1H, s, N—H) (Found: C, 54.13; H, 6.44; N, 16.19%; M$^+$ 421.1958; $C_{19}H_{27}N_5O_6$ requires C, 54.15; H, 6.46; N, 16.62%; M$^+$ 421.1961).

The second compound to elute was 9-(4-propionyloxy-3-propionyloxymethylbut-1-yl)guanine (150 mg, 41%) which was recrystallised from methanol, m.p. 204–206° C.; vmax (KBr) 3310, 3150, 1740, 1690, and 1190 $cm^{-1}$; $δ_H$ [$(CD_3)_2SO$] 1.01 (6H, t, J 7.4 Hz, 2×CH$_2$CH$_3$), 1.80 (2H, q, J 7.0 Hz, CHCH$_2$CH$_2$), 1.91 (1H, m, CHCH$_2$CH$_2$), 2.29 (4H, q, J 7.5 Hz, 2×CH$_2$CH$_3$), 4.01 (6H, m, 2×CH$_2$O and CH$_2$N), 6.37 (2H, s, D$_2$O exchangeable, 2-NH$_2$), 7.69 (1H, s, 8-H), and 10.50 (1H, s, D$_2$O exchangeable, 1-H) (Found: C, 52.28; H, 6.20; N, 18.95%; $C_{16}H_{23}N_5O_5$ requires C, 52.59; H, 6.35; N, 19.17%).

EXAMPLE 25

9-(4-Hexanoyloxy-3-hexanoyloxymethylbut-1-yl)guanine

A mixture of 9-(4-hydroxy-3-hydroxymethylbut-1-yl)guanine (253 mg, 1.0 mmol), dicyclohexylcarbodiimide (0.83 g, 4.0 mmol), hexanoic acid (0.38 ml, 0.35 g, 3.0 mmol), 4-dimethylaminopyridine (20 mg) and N,N-dimethylformamide (5 ml) was stirred for 64 hours at room temperature. The mixture was diluted with water and extracted with chloroform (×2). The combined organic layers were washed with aqueous sodium bicarbonate, dried (magnesium sulphate) and the solvent removed. The residue was purified by column chromatography eluting with chloroform-methanol mixtures to afford 9-(4-hexanoyloxy-3-hexanoyloxymethylbut-1-yl)guanine (200 mg, 45%) which was recrystallised from methanol, m.p. 198.5–201° C.; λmax (KBr) 3340, 3160, 2930, 1740, 1690, 1650, 1605, and 1170 $cm^{-1}$; $δ_H$ (CDCl$_3$) 0.87 (6H, t, J 6.9 Hz, 2×CH$_3$), 1.28 (8H, m, 2×CH$_2$CH$_2$CH$_3$), 1.60 (4H, quintet, J 7.4 Hz, 2×COCH$_2$CH$_2$), 1.90 (2H, q, J 6.9 Hz, CHCH$_2$CH$_2$N), 2.02 (1H, m, CHCH$_2$CH$_2$N), 2.30 (4H, t, J 7.6 Hz, 2×COCH$_2$CH$_2$), 4.13 (6H, m, 2×CH$_2$O and CH$_2$N), 6.42 (2H, s, D$_2$O exchangeable, 2-NH$_2$), 7.70 (1H, s, 8-H), and 12.16 (1H, s, D$_2$O exchangeable, 1-H) (Found: C, 53.97; H, 7.92; N, 15.45%; $C_{22}H_{35}N_5O_5$ requires C, 58.78; H, 7.85; N. 15.58%).

EXAMPLE 26

9-(4-Formyloxy-3-formyloxymethylbut-1-yl)guanine

A mixture of 9-(4-hydroxy-3-hydroxymethylbut-1-yl)guanine (0.23 g, 0.9 mmol), dicyclohexylcarbodiimide (0.92 g, 4.5 mmol), formic acid (0.17 ml, 4.5 mmol), 4-dimethylaminopyridine (20 mg) and N,N-dimethylformamide (5 ml) was stirred for 40 minutes at room temperature and then quenched by addition of methanol (1 ml). The solution was filtered and the solvent removed. The residue was purified by column chromatography on silica gel eluting with chloroform-methanol mixtures (7:1, 4:1) to afford 9-(4-formyloxy-3-formyloxymethylbut-1-yl)guanine which was crystallised from methanol (0.12 g, 43%), m.p. 195–198° C.; vmax (KBr) 1720, 1680, 1630, 1600, and 1570 $cm^{-1}$; $δ_H$ [$(CD_3)_2SO$] 1.83 (2H, q, J 7.1 Hz, 2'-H), 2.01 (1H, m, 3'-H), 4.04 (2H, t, J 7.1 Hz, 1'-H), 4.13 (4H, d, J 5.5 Hz, 2×4'-H), 6.39 (2H, s, D$_2$O exchangeable, 2-NH$_2$), 7.70 (1H, s, 8-H), 8.23

(2H, s, 2×HCOO), and 10.52 (1H, s, $D_2O$ exchangeable, 1-H); (Found: C, 45.40; H, 4.68; N, 21.70%; $C_{12}H_{15}N_5O_5$ requires: C, 46.60; H, 4.89; N, 22.64%).

EXAMPLE 27

9-[4-(N-Imidazolylcarbonyloxy)-3-(N-imidazolylcarbonyloxymethyl)but-1-yl]guanine A mixture of 9-(4-hydroxy-3-hydroxymethlbut-1-yl)guanine (253 mg, 1.0 mmol), N,N'-carbonyldiimidazole (187 mg, 1.15 mmol), 4-dimethylaminopyridine (20 mg) and N,N-dimethylformamide (5 ml) was stirred at room temperature. After 2 hours a further quantity of N,N'-carbonyldiimidazole (180 mg) was added and stirring was continued for a further 2 hours. The solvent was removed and the residue washed with water, ethyl acetate and hot methanol leaving 9-[4-(N-Imidazolylcarbonyloxy)-3-(N-imidazolylcarbonyloxymethyl)but-1-yl]guanine (360 mg, 82%), m.p. >300° C.; νmax (KBr) 3320, 3140, 1760, 1695, 1630, and 1600 cm$^{-1}$; $\delta_H$ [$(CD_3)_2SO$] 2.0 (2H, q, J 7 Hz, CHC$\underline{H}_2$CH$_2$), 2.15–2.40 (1H, m, C$\underline{H}$CH$_2$CH$_2$), 4.10 (2H, t, J 7 Hz, CH$_2$), 4.48 (4H, d, J 5 Hz, 2×CH$_2$O), 6.32 (1H, s, $D_2O$ exchangeable, 2-NH$_2$), 7.05 (2H, s, imid-H), 7.57 (2H, s, imid-H), 7.75 (1H, s, 8-H), 8.28 (2H, s, imid-H), and 10.53 (1H, s, $D_2O$ exchangeable, 1-H); M/Z 68 (100, imidazole$^+$), (70, $CO_2{}^+$), 41 (72, NCHN$^+$).

EXAMPLE 28 & 29

$N^2$-Monomethoxytrityl-9-(4-monomethoxytrityloxy-3-hydroxymethylbut-1-yl)guanine and $N^2$-Monomethoxytrityl-9-(4-hydroxy-3-hydroxymethylbut-1-yl)guanine A solution of 9-(4-hydroxy-3-hydroxymethylbut-1-yl)guanine (4.05 g, 16 mmol), monomethoxytrityl chloride (10.9 g 35 mmol), triethylamine (6.7 ml) and 4-dimethylaminopyridine (40 mg) in N,N-dimethylformamide (50 ml) was stirred for 2 hours. The reaction was quenched with methanol and the solvent was removed. The residue was taken up in ethyl acetate and the solution washed with aqueous sodium bicarbonate and water. The solution was dried (magnesium sulphate) and the solvent removed. The residue was purified by column chromatography on silica gel eluting with chloroform-methanol mixtures. The first major product to elute was $N^2$-monomethoxytrityl-9-(4-monomethoxytrityloxy-3-hydroxymethylbut-1-yl)guanine (4.4 g, 34%), m.p. 142–145° C.; λmax (EtOH) 230 (sh. 29,900) and 262 (16,000) nm; νmax (KBr) 3400, 1680, 1605, 1570, and 1510 cm$^{-1}$; $\delta_H$[$(CD_3)_2SO$] 1.24 (2H, m, 2'-H), 1.43 (1H, m, 3'-H), 2.7–2.9 (2H, AB part of ABX, CH$_2$OC), 3.1–3.4 (2H, AB part of ABX C$\underline{H}_2$OH), 3.42 (2H, t, J 6.7 Hz, 1'-H), 3.66 (3H, s, CH$_3$O), 3.74 (3H, s, CH$_3$O), 4.35 (1H, t, J 4.8 Hz, $D_2O$ exchangeable, OH), 6.7–7.4 (28H, m, Ar—H), 7.44 (1H, s, 8-H), 7.55 (1H, s, $D_2O$ exchangeable, 2-NH), and 10.50 (1H, s, $D_2O$ exchangeable, 1-H); (Found: C, 74.28; H, 5.86; N, 8.64%; $C_{50}H_{47}N_5O_5$ requires: C, 75.26; H, 5.94; N, 8.78%).

The second major product to elute was $N^2$-monomethoxytrityl-9-(4-hydroxy-3-hydroxymethylbut-1-yl)guanine (1.4 g, 17%), m.p. 205–207° C.; λmax (EtOH) 261 (14,500) nm; νmax (KBr) 3380, 1705, 1680, 1610, 1570, and 1515 cm$^{-1}$; $\delta_H$[$(CD_3)_2SO$] 1.25 (3H, m, 2'-H and 3'-H), 3.1–3.3 (4H, m, 2×4'-H), 3.52 (2H, t, J 6.6 Hz, 1'-H), 3.72 (3H, s, CH$_3$O), 4.28 (2H, t, J 5.2 Hz, $D_2O$ exchangeable, 2×OH), 6.85–7.35 (14H, m, Ar—H), 7.54 (1H, s, 8-H), 7.56 (1H, s, $D_2O$ exchangeable, 2-NH), and 10.49 (1H, s, $D_2O$ exchangeable, 1-H); (Found: C, 67.93; H, 6.05; N, 12.90%; $C_{30}H_{31}N_5O_4$ requires C, 68.55; H, 5.95; N, 13.32%).

EXAMPLE 30

9-(4-Pivalyloxy-3-pivalyloxymethylbut-1-yl)guanine

To a solution of $N^2$-monomethoxytrityl-9-(4-hydroxy-3-hydroxymethylbut-1-yl)guanine (0.47 g, 0.9 mmol) in pyridine (4.5 ml) was added pivalyl chloride (0.55 ml, 4.5 mmol) and the solution was stirred for 45 minutes. The mixture was precipitated in water (45 ml) and the resulting precipitate was stirred in 80% acetic acid (10 ml) at 80° for 20 minutes. The solvent was removed and the residue was purified by column chromatography on silica gel eluting with chloroform-methanol (10:1) to afford 9-(4-pivalyloxy-3-pivalyloxymethylbut-1-yl)guanine (0.22 g, 58%), m.p. 225–237° C.; νmax (KBr) 3430, 2980, 1730, 1690, and 1620 cm$^{-1}$; $\delta_H$ [$(CD_3)_2SO$] 1.11 (18H, s, 2×C(CH$_3$)$_3$), 1.81 (2H, q, J 6.8 Hz, 2'-H), 1.93 (1H, m, 3'-H), 4.0–4.1 (6H, m, 1'-H and 2×4'-H), 6.38 (2H, s, 2-NH$_2$), 7.69 (1H, s, 8-H), and 10.58 (1H, br.s, 1-H); (Found: C, 56.58; H, 7.26; N, 16.14%; $C_{20}H_{31}N_5O_5$ requires: C, 56.99; H, 7.41; N, 16.62%).

EXAMPLE 31

9-(4-Acetoxy-3-hydroxymethylbut-1-yl)guanine

To a solution of $N^2$-monomethoxytrityl-9-(4-monomethoxytrityloxy-3-hydroxymethylbut-1-yl)guanine (0.72 g, 0.9 mmol) in pyridine (3 ml) was added acetyl chloride (0.21 ml, 3.0 mmol) and the solution was stirred for 30 minutes. The mixture was precipitated in water (30 ml) the resulting precipitate was stirred in 80% acetic acid (10 ml) at 80° for 30 minutes. The solvent was removed and the residue purified by column chromatography on silica gel eluting with chloroform-methanol mixtures (7:1, 3:1) to afford 9-(4-acetoxy-3-hydroxymethylbut-1-yl)guanine (0.17 g, 64%), m.p. 194–200° C.; νmax (KBr) 3330, 3170, 2930, 1730, 1690, 1660, 1610, and 1565 cm$^{-1}$; $\delta_H$ [$(CD_3)_2SO$] 1.6–1.8 (3H, m, 2'-H and 3'-H), 1.98 (3H, s, CH$_3$), 3.39 (2H, br, $D_2O$ exchange gives d, J 5 Hz, C$\underline{H}_2$OH), 3.9–4.1 (4H, m, 1'-H and CH$_2$OCO), 4.61 (1H, br.t, $D_2O$ exchangeable, OH), 6.44 (2H, s, $D_2O$ exchangeable, 2-NH$_2$), 7.68 (1H, s, 8-H), and 10.59 (1H, s, $D_2O$ exchangeable, 1-H); (Found: C, 47.91; H, 5.63; N, 21.71%; $C_{12}H_{17}N_5O_4$ requires: C, 48.81; H, 5.80; N, 23.72%).

EXAMPLE 32

9-(4-Benzoyloxy-3-hydroxymethylbut-1-yl)guanine

To a solution of $N^2$-monomethoxytrityl-9-(4-monomethoxytrityloxy-3-hydroxymethylbut-1-yl)guanine (0.72 g, 0.9 mmol) in pyridine (4 ml) was added benzoyl chloride (0.31 ml, 2.7 mmol) and the solution was stirred for 30 minutes. The mixture was precipitated in water (40 ml) and the resulting precipitate was stirred in 80% acetic acid (10 ml) at 80° for 45 minutes. The solvent was removed and the residue purified by column chromatography on silica gel eluting with chloroform-methanol mixtures (6:1, 3:1) to afford 9-(4-benzoyloxy-3-hydroxymethylbut-1-yl)guanine (80 mg, 25%), m.p. 156–168° C; λmax (MeOH) 231 (15, 100) and 254 (13,100) nm; νmax (KBr) 1715, 1690, 1625, and 1600 cm$^{-1}$; $\delta_H$ [$(CD_3)_2SO$] 1.75–1.90 (3H, m, 2'-H and 3'-H), 3.50 (2H, t, J 5 Hz, $D_2O$ exchange leaves d, C$\underline{H}_2$OH), 4.07 (2H, t, J 6.9 Hz, 1'-H), 4.2–4.35 (2H, AB part of ABX, CH$_2$OCO), 4.68 (1H, t, J 5.1 Hz, D$_2$O exchangeable, OH), 6.39 (2H, s, D$_2$O exchangeable, 2-NH$_2$), 7.5–8.0 (6H, m, C$_6$H$_5$ and 8-H), and 10.53 (1H, s, D$_2$O exchangeable, 1-H); (Found: C, 53.57; H, 5.28; N, 17.95%; C$_{17}$H$_{19}$N$_5$O$_4$.0.25 CHCl$_3$ requires: C, 53.51; H, 5.01; N, 18.09%).

EXAMPLE 33

9-(4-Hexanoyloxy-3-hydroxymethylbut-1-yl) guanine

To a solution of N$^2$-monomethoxytrityl-9-(4-monomethoxytrityloxy-3-hydroxymethylbut-1-yl)guanine (0.72 g, 0.9 mmol) in pyridine (4 ml) was added hexanoyl chloride (0.38 ml, 2.7 mmol) and the solution was stirred for 20 minutes. The mixture was precipitated in water (40 ml) and the resulting precipitate was stirred in 80% acetic acid (10 ml) at 80° for 45 minutes. The solvent was removed and the residue purified by column chromatography on silica gel eluting with chloroform-methanol mixtures (7:1, 5:1) to afford 9-(4-hexanoyloxy-3-hydroxymethylbut-1-yl)guanine (0.12 g, 38%), m.p. 179–181° C.; vmax 2960, 2930, 1730, 1690, 1630, and 1600 cm$^{-1}$; δ$_H$ [(CD$_3$)$_2$SO] 0.84 (3H, t, J 6.9 Hz, CH$_3$), 1.24 (4H, m, CH$_3$(CH$_2$)$_2$), 1.50 (2H, quintet, J 7.3 Hz, CH$_2$CH$_2$CO), 1.6–1.8 (3H, m, 2'-H and 3'-H), 2.26 (2H, t, J 7.3 Hz, CH$_2$CO), 3.40 (2H, t, J 5 Hz, D$_2$O exchange leaves d, CH$_2$OH), 3.9–4.1 (4H, m, 1'-H and CH$_2$OCO), 4.60 (1H, t, J 5.1 Hz, D$_2$O exchangeable, 2-NH$_2$), 7.67 (1H, s, 8-H), and 10.49 (1H, s, D$_2$O exchangeable, 1-H); (Found: C, 52.63; H, 6.91; N, 18.75%; C$_{16}$H$_{25}$N$_5$O$_4$ requires: C, 54.69; H, 7.17; N, 19.93%).

EXAMPLE 34

9-(4-Hexadecanoyloxy-3-hydroxymethylbut-1-yl) guanine

To a solution of N$^2$-monomethoxytrityl-9-(4-monomethoxytrityloxy-3-hydroxymethylbut-1-yl)guanine (0.72 g, 0.9 mmol) in pyridine (4 ml) was added hexadecanoyl chloride (0.82 ml, 2.7 mmol) and the solution was stirred for 30 minutes. The mixture was precipitated in water (40 ml) and the resulting precipitate was stirred in 80% acetic acid (8 ml) at 80° for 2 hours. The solvent was removed and the residue was purified by column chromatography on silica gel eluting with chloroform-methanol mixtures (10:1, 8:1) to afford 9-(4-hexadecanoyloxy-3-hydroxymethylbut-1-yl)guanine (0.23 g, 52%), m.p. 183–191° C.; vmax (KBr) 3340, 3160, 2920, 2850, 1740, 1690, and 1605 cm$^{-1}$; δ$_H$ [(CD$_3$)$_2$SO] 0.85 (3H, t, J 6.6 Hz, CH$_3$), 1.23 (24H, m, CH$_3$(CH$_2$)$_{12}$), 1.49 (2H, m, CH$_2$CH$_2$CO), 1.6–1.8 (3H, m, 2'-H and 3'-H), 2.26 (2H, t, J 7.3 Hz, CH$_2$CO), 3.39 (2H, t, J 5 Hz, D$_2$O exchange leaves d, CH$_2$OH), 3.9–4.1 (4H, m, 1'-H and CH$_2$OCO), 4.60 (1H, t, J 5.2 Hz, D$_2$O exchangeable, OH), 6.38 (2H, s, D$_2$O exchangeable, 2-NH$_2$), 7.67 (1H, s, 8-H), and 10.50 (1H, s, D$_2$O exchangeable, 1-H); (Found: C, 63.83; H, 9.44; N, 14.05%; C$_{26}$H$_{45}$N$_5$O$_4$ requires: C, 63.51; H, 9.23; N, 14.24%).

EXAMPLE 35

9-(4-Hydroxy-3-hydroxymethylbut-1-yl)guanine 4'-phosphate diammonium salt

To a solution of cyanoethyl phosphoric acid (4.8 mmol) in pyridine (6 ml) were added N$^2$-monomethoxytrityl-9-(4-monomethoxytrityloxy-3-hydroxymethylbut-1-yl)guanine (1.28 g, 1.6 mmol) and dicyclohexylcarbodiimide (1.98 g, 9.6 mmol) and the solution was stirred for 2 hours. Reaction was quenched by addition of water (1 ml) and the solvent was removed. To the residue was added concentrated aqueous ammonia and the mixture was stirred at 60° for 3 hours. The solvent was removed and to the residue was added 80% acetic acid (15 ml). The mixture was stirred at 80° for 45 minutes and the solvent was removed. The residue was taken up in water (25 ml) and extracted with chloroform (4×30 ml). The aqueous layer was filtered, concentrated and passed down a column of XAD-4 resin, eluting with aqueous methanol mixtures. Fractions containing product were pooled and the solvent removed. The residue was taken up in a small volume of water and the solution was passed through C$_{18}$-Sep-pak cartridges. Fractions containing product were pooled and the solvent removed to afford 9-(4-hydroxy-3-hydroxymethylbut-1-yl)guanine 4'-phosphate, diammonium salt as a white solid (0.31 g, 53%); vmax (KBr) 3150 (broad), 1690, and 1610 cm$^{-1}$; δ$_H$ [(CD$_3$)$_2$SO/D$_2$O] 1.57 (1H, m, 3'-H), 1.70 (2H, m, 2'-H), 3.37 (2H, d, J 4.7 Hz, CH$_2$OH), 3.72 (2H, m, CH$_2$OP), 3.99 (2H, t, J 6.9 Hz, 1'-H), and 7.68 (1H, s, 8-H).

EXAMPLE 36

N$^2$-Acetyl-9-(4-hydroxy-3-hydroxymethylbut-1-yl) guanine

To a suspension of 9-(4-hydroxy-3-hydroxymethylbut-1-yl)guanine (0.23 g, 0.9 mmol) in pyridine (3 ml) was added chlorotrimethylsilane (0.25 ml, 2.0 mmol) and the mixture was stirred for 15 minutes. To this mixture was added acetyl chloride (0.085 ml, 1.2 mmol) and the mixture was stirred for 30 minutes. Methanol (2 ml) was the added and the mixture was stirred for a further 30 minutes. The solvent was removed and the residue purified by column chromatography on silica gel eluting with chloroform-methanol mixtures (4:1, 5:2) to give the title compound as its hydrochloride salt. This was dissolved in methanol and stirred with potassium carbonate. The solution was filtered and the solvent removed. The residue was taken up in water and passed through C$_{18}$-Sep-pak cartridges. Fractions containing product were pooled and the solvent removed to afford N$^2$-acetyl-9-(4-hydroxy-3-hydroxymethylbut-1-yl)guanine (0.11 g, 41%), m.p. 143–146° C.; λmax (H$_2$O) 260 (15,100) nm; vmax (KBr) 3420, 3200, 2940, 1685, 1615, and 1560 cm$^{-1}$; δ$_H$ [(CD$_3$)$_2$SO] 1.46 (1H, m, 3'-H), 1.77 (2H, q, J 7.1 Hz, 2'-H), 2.18 (3H, s, CH$_3$), 3.3–3.5 (4H, m, 2×4'-H), 4.13 (2H, t, J 7.4 Hz, 1'-H), 4.42 (2H, br.t, J 5 Hz, D$_2$O exchangeable, 2×OH), 7.98 (1H, s, 8-H), and 11.83 (2H, br, D$_2$O exchangeable, 1-H and 2-NH).

EXAMPLE 37

N$^2$-Hexanoyl-9-(4-hydroxy-3-hydroxymethylbut-1-yl)guanine

To a suspension of 9-(4-hydroxy-3-hydroxymethylbut-1-yl)guanine (0.25 g, 1.0 mmol) in pyridine (5 ml) was added chlorotrimethylsilane (0.32 ml, 2.5 mmol) and the mixture was stirred for 15 minutes. To this mixture was added hexanoyl chloride (0.18 ml, 1.3 mmol) and the mixture was stirred for 20 minutes. Methanol (2 ml) was then added and the mixture was stirred for a further 20 minutes. 1,8-Diazabicyclo[5.4.0]-undec-7-ene (0.57 ml, 3.8 mmol) and water (0.5 ml) were added and the solvent was removed. The residue was purified by column chromatography on silica gel eluting with chloroform-methanol (4:1). Product containing fractions were pooled and the solvent removed. The residue was taken up in water and passed through C$_{18}$-Seppak cartridges to afford $N^2$-hexanoyl-9-(4-hydroxy-3-hydroxymethylbut-1-yl)guanine (50 mg, 14%), m.p. 86–88° C.; vmax (KBr) 3400, 2960, 2940, 1675, 1610, and 1560 cm$^{-1}$; $\delta_H$ [(CD$_3$)$_2$SO] 0.88 (3H, t, J 6.7 Hz, CH ) 1.29 (4H, m, CH$_3$(C$\underline{H}_2$)$_2$), 1.46 (1H, m, 3'-H), 1.60 (2H, m, C $\underline{H}_2$CH$_2$CO), 1.77 (2H, q, J 7.1 Hz, 2'-H), 2.46 (2H, t, J 7.4 Hz, CH$_2$CO) 3.3–3.5 (4H, m, 2×4'-H), 4.13 (2H, t, J 7.4 Hz, 1'-H), 4.41 (2H, t, J 4.7 Hz, D$_2$O exchangeable, 2×OH), 7.98 (1H, s, 8-H), 11.65 (1H, br, D$_2$O exchangeable, NH), and 12.01 (1H, br, D$_2$O exchangeable, NH); (Found: C, 53.64; H, 7.56; N, 18.95%; C$_{16}$H$_{25}$N$_5$O$_4$.0.5H$_2$O requires: C, 53.32; H, 7.27; N, 19.43%).

EXAMPLE 38

2-Amino-9-(4-hydroxy-3-hydroxymethylbut-1-yl)-6-isopropoxypurine

A solution of 2-amino-6-chloro-9-[2-(2,2-dimethyl-1,3-dioxan-5-yl)ethyl]purine (0.25 g, 0.8 mmol) in isopropanol (2.5 ml) containing sodium isopropoxide (0.5M) was stirred at 60° for 25 minutes. After cooling, hydrochloric acid (5M, 0.3 ml) and water (0.7 ml) were added and the solution was stirred for 15 minutes at room temperature. The solution was neutralised by addition of aqueous.sodium bicarbonate and the solvent was removed. The residue was extracted with chloroform-ethanol (2:1) and the solution purified by column chromatography on silica gel eluting with chloroform-methanol (7:1) to afford 2-amino-9-(4-hydroxy-3-hydroxymethylbut-1-yl)-6-isopropoxypurine which was crystallised from chloroform-carbon tetrachloride (0.18 g, 76%), m.p. 111.5–113.5° C., $\delta_H$ [(CD$_3$)$_2$SO] 1.34 (6H, d, J 6.3 Hz, C(CH$_3$)$_2$), 1.45 (1H, m, 3'-H), 1.74 (2H, q, J 7.2 Hz, 2'-H), 3.3–3.5 (4H, AB part of ABX, 2×4'-H), 4.06 (2H, t, J 7.3 Hz, 1'-H), 4.40 (2H, br, 2×OH), 5.49 (1H, septet, J 6.3 Hz, C$\underline{H}$(CH$_3$)$_2$), 6.27 (2H, s, 2-NH$_2$), and 7.83 (1H, s, 8-H).

EXAMPLE 39

2-Amino-9-(4-hydroxy-3-hydroxymethylbut-1-yl)-6-phenoxypurine

To a solution of phenol (113 mg, 1.2 mmol) in dry dioxan (2.5 ml) was added sodium hydride (60% dispersion in oil; 48 mg, 1.2 mmol). After evolution of hydrogen ceased, 2-amino-6-chloro-9-[2-(2,2-dimethyl-1,3-dioxan-5-yl)ethyl]purine (0.25 g, 0.8 mmol) was added and the mixture was stirred at 75° for 3.5 hours. After cooling, water (0.8 ml) and hydrochloric acid (5M, 0.2 ml) were added and the solution was stirred for 30 minutes at room temperature. The solution was neutralised by addition of aqueous sodium bicarbonate and the solvent was removed. The residue was extracted with chloroform-ethanol (2:1) and the solution purified by column chromatography on silica gel eluting with chloroform-methanol (9:1) to afford 2-amino-9-(4-hydroxy-3-hydroxymethylbut-1-yl)-6-phenoxypurine (145 mg, 55%), m.p. 173–175° C.; $\delta_H$ [(CD$_3$)$_2$SO] 1.48 (1H, m, 3'-H), 1.78 (2H, q, J 7.1 Hz, 2'-H), 3.3–3.5 (4H, m, 2×4'-H), 4.12 (2H, t, J 7.4 Hz, 1'-H), 4.42 (2H, t, J 5.1 Hz, D$_2$O exchangeable, 2×OH), 6.35 (2H, s, D$_2$O exchangeable, 2-NH$_2$), 7.2–7.5 (5H, m, C$_6$H$_5$), and 7.98 (1H, s, 8-H).

Example of Pharmaceutical Activity

Method 1

Vero (Arican Green Monkey Kidney) cells were grown to confluence in 24 well multidishes, each well being 1.6 cm in diameter. The cells were infected with Herpes simplex type 1 virus (HFEM strain) and overlaid with 0.5 ml of 0.9% agarose (w/v) in maintenance medium. The test compound, prepared in maintenance medium in concentrations ranging from 100 to 0.3 $\mu$g/ml in half-log dilution steps, was added in 0.5 ml volume. The virus infected cultures were then incubated at 37° C. for 4 days before fixing in 4% formaldehyde solution and staining with carbol fuchsin. The dishes were then examined to find what concentration of test compound caused a 50% reduction in the number of virus plaques formed (PDD$_{50}$ value) and the minimum concentration of test compound which caused cytotoxicity (MTD).

Method 2

MRC-5 cells were infected in suspension with Herpes simplex type 1 virus, strain SC16. The infected cell suspension was dispensed (0.1 ml) in 96 well microtitre plates containing the test drugs in maintenance medium in concentrations ranging from 100 to 0.03 $\mu$g/ml in half-log dilution steps (0.1 ml per well). The plates were then icubated at 37° C. for 3 days when the virus cytopathic effect (CPE) in the control wells reached 100%. The plates were fixed in 4% formaldehyde solution and stained with carbol fuchsin. The plates were then examined to find what concentration of test compound recuced the virus CPE by 50% (IC$_{50}$). Plates using uninfected cells were run in parallel to determine the minimum concentration of test compound which caused cytotoxicity (MTD).

Compounds were also tested against Herpes simplex type 2 virus (MS strain) in Vero cells using Method 1 and in MRC-5 cells using Method 2. In the latter test, the incubation time was reduced to 24 hours.

Results

PDD$_{50}$ ($\mu$g/ml)

| | Herpes simplex type 1 virus | | Herpes simplex type 2 virus | |
|---|---|---|---|---|
| Example No. | HFEM strain in Vero cells | SC16 strain in MRC-5 cells | MS strain in Vero cells | MS strain in MRC-5 cells |
| 4 | 1.3 | 0.9 | 2.3 | 0.6 |
| 12 | 2.2 | 0.7 | | |
| 13 | 1.7 | 0.7 | | |
| 15 | >100 | >100 | 63 | 49 |
| 22 | >100 | >100 | >100 | 83 |
| 23 | >100 | 25 | >100 | 85 |
| 24 | >100 | >100 | >100 | 65 |
| 25 | 1.9 | 1.0 | 1.6 | 0.9 |
| 27 | 13 | 1.5 | 2.8 | 5.7 |
| 31 | 24 | 10 | | |
| 32 | 95 | 3 | | |
| 34 | 16 | 2 | | |

None of the compounds was cytotoxic at concentrations up to 100 $\mu$g/ml in any of the tests.

Method 3

Compounds were administered by oral gavage (0.2 mmoles/kg in 0.1 ml of 1% carboxymethyl cellulose) to 20 g female Balb/C mice which had been starved for 18 hours. Fifteen minutes later, blood was collected from three mice by cardiac puncture using heparinised syringes. Equal aliquots were pooled and an equal volume of 16% trichloroacetic acid added. Following centrifugation (8,500 g) to remove precipitated proteins, the resulting mixture was analysed by high performance liquid chromatography using a C$_{18}$ Nova-Pak cartridge eluted with Buffer A (50 mM NaH$_2$PO$_4$, pH$_{4.6}$) and Buffer B (10% Buffer A, 10% water, 80% methanol) in a gradient from 1% to 95% Buffer B. 9-(4-Hydroxy-3-hydroxymethylbut-1-yl) guanine was assayed with a Pye-Unicam PU4021 u.v. detector set at 254 nm.

Results
Concentrations of 9-(4-Hydroxy-3-hydroxymethylbut-1-yl)
guanine (Example 4) in the Blood of Mice After Oral
Administration of Derivatives

| Administered compound | Concentration of Example 4 in Blood (μg/ml) |
|---|---|
| Example 15 | 0.2 |
| Example 16 | 2.3 |
| Example 17 | 4.8 |
| Example 22 | 2.0 |
| Example 23 | 2.5 |
| Example 30 | 0.3 |
| Example 35 | 1.1 |

What is claimed is:

1. A pharmaceutical composition comprising a compound of formula A:

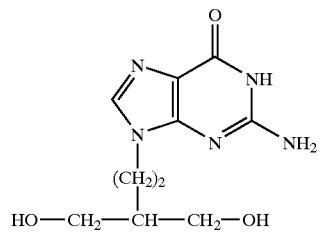

[(III)]A or pharmaceutically acceptable salt thereof, and a pharmaceutically acceptable carrier or excipient.

2. A pharmaceutical composition as recited in claim 1 wherein said salt of said compound is the sodium salt.

3. A method of treating herpesvirus infections in a human in need thereof, which method comprises administering to said human an effective, non-toxic dose of a pharmaceutical composition as recited in claim 1.

4. A method of treating herpesvirus infections in a human in need thereof, which method comprises administering to said human an effective, non-toxic dose of a pharmaceutical composition as recited in claim 2.

5. A method of treating a herpesvirus infection wherein said infection is a herpes simplex type 1 (HSV-1) virus infection in a human or animal in need thereof, which method comprises administering to said human or animal an effective, non-toxic dose of a pharmaceutical composition as recited in claim 1.

6. A pharmaceutical composition as recited in claim 1 which is suitable for topical application.

7. A pharmaceutical composition as recited in claim 6 suitable for application to the skin.

8. A method of treating herpesvirus infections in an animal in need thereof, which method comprises administering to said animal an effective amount of a pharmaceutical composition as recited in claim 1.

9. A method as recited in claim 8 wherein the compound is administered by injection.

10. A method as recited in claim 8 wherein the compound is administered topically.

11. A method as recited in claim 10 wherein the compound administered to the eyes.

12. A method as recited in claim 10 wherein the compound administered to the skin.

13. A method as recited in claim 12 wherein the compound is in a cream formulation.

14. A method of treating herpesvirus infections in an animal in need thereof, which method comprises administering to said animal an effective amount of a pharmaceutical composition as recited in claim 2.

15. A method as recited in claim 14 wherein the compound is administered by injection.

16. A method as recited in claim 14 wherein the compound is administered topically.

17. A method as recited in claim 16 wherein the compound is administered to the eyes.

18. A method as recited in claim 16 wherein the compound is administered to the skin.

19. A method as recited in claim 18 wherein the compound is in a cream formulation.

20. A method of treating a herpesvirus infection, wherein said infection is a herpes simplex type 1 (HSV-1) virus infection, in a human or animal in need thereof, which method comprises administering to said human or animal an effective, non-toxic dose of a compound of the formula

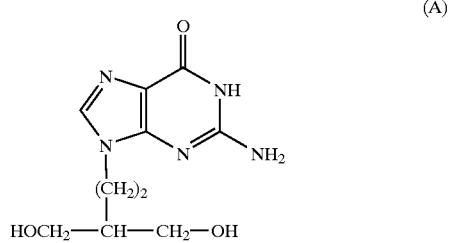

(A)

or a pharmaceutically acceptable salt thereof.

21. A method of treating a herpesvirus infection, wherein said infection is a herpes simplex type 2 (HSV-2) virus infection, in a human or animal in need thereof, which method comprises administering to said human or animal an effective, non-toxic dose of a compound of the formula

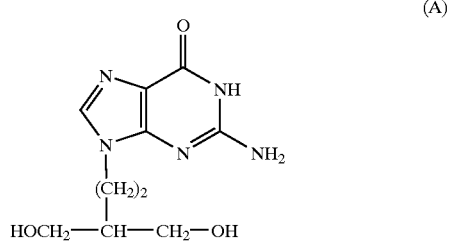

(A)

or a pharmaceutically acceptable salt thereof.

22. A method of treating a herpesvirus infection, wherein said infection is a varciella zoster (VZV) virus infection, in a human or animal in need thereof, which method comprises administering to said human or animal an effective, non-toxic dose of a compound of the formula

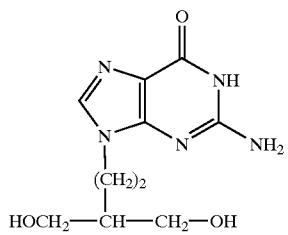
(A)

or a pharmaceutically acceptable salt thereof.

23. A method as recited in claim 3 wherein the compound is administered by injection.

24. A method as recited in claim 3 wherein the compound is administered topically.

25. A method as recited in claim 24 wherein the compound is administered to the eyes.

26. A method as recited in claim 24 wherein the compound is administered to the skin.

27. A pharmaceutical composition comprising a sodium salt of a compound of the formula

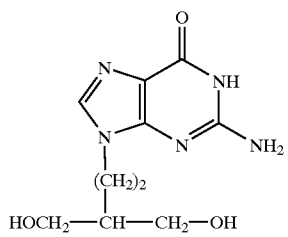
(A)

and a pharmaceutically acceptable carrier or excipient, said compound having a purity of greater than 90% by weight.

28. A method as recited in claim 4 wherein the compound is administered by injection.

29. A method as recited in claim 4 wherein the compound is administered topically.

30. A method as recited in claim 4 wherein the compound is administered to the eyes.

31. A method as recited in claim 29, wherein the compound is administered to the skin.

32. A method as recited in claim 31 wherein the compound is in a cream formulation.

33. A method as recited in claim 5 wherein the compound is administered by injection.

34. A method as recited in claim 5 wherein the compound is administered topically.

35. A method as recited in claim 5 wherein the compound is administered to the eyes.

36. A method as recited in claim 34 wherein the compound is administered to the skin.

37. A method as recited in claim 36 wherein the compound is in a cream formulation.

38. A pharmaceutical composition as recited in claim 27 which is suitable for topical application.

39. A pharmaceutical composition as recited in claim 2 which is suitable for injection.

40. A pharmaceutical composition as recited in claim 7 formulated as a cream.

41. A method of treating a herpesvirus infection wherein said infection is a herpes simplex type 2 (HSV-2) virus infection in a human or animal in need thereof, which method comprises administering to said human or animal an effective, non-toxic dose of a pharmaceutical composition as recited in claim 1.

42. A method of treating a herpesvirus infection wherein said infection is a varicella zoster virus (VZV) virus infection in a human or animal in need thereof, which method comprises administering to said human or animal an effective, non-toxic dose of a pharmaceutical composition as recited in claim 1.

43. A method of treating herpesvirus infections in a human or animal in need thereof, which method comprises administering to said human or animal an effective, non-toxic dose of a compound of the formula

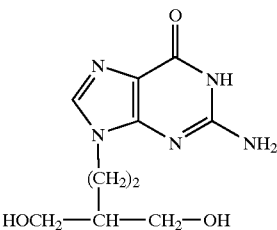
(A)[A]

or a pharmaceutically acceptable salt thereof.

44. A method as recited in claim 43 wherein said pharmaceutically acceptable salt is the sodium salt.

45. A method as recited in claim 26 wherein the compound is in a cream formulation.

46. A pharmaceutical composition as recited in claim 27 which is suitable for injection.

47. A pharmaceutical composition as recited in claim 38 suitable for application to the eyes.

48. A pharmaceutical composition as recited in claim 38 suitable for application to the skin.

49. A pharmaceutical composition as recited in claim 48 in the form of a cream.

50. A pharmaceutical composition as recited in claim 42 suitable for application to the eyes.

* * * * *

UNITED STATES PATENT AND TRADEMARK OFFICE
CERTIFICATE OF CORRECTION

PATENT NO.    : 6,579,981 B1
DATED         : June 17, 2003
INVENTOR(S)   : Jarvest et al.

It is certified that error appears in the above-identified patent and that said Letters Patent is hereby corrected as shown below:

<u>Title page,</u>
Item [30], Foreign Application Priority Data, should read:
-- Aug. 18, 1983    (GB) ..........................8322199
   Sep. 21, 1983    (GB) ..........................8325271
   Mar. 30, 1984    (GB) ..........................8408322 --

<u>Column 28,</u>
Line 50, should read: -- 50. A pharmaceutical composition as recited in claim 6 --

Signed and Sealed this

Thirtieth Day of September, 2003

JAMES E. ROGAN
*Director of the United States Patent and Trademark Office*